United States Patent
Wang

(10) Patent No.: US 10,074,257 B2
(45) Date of Patent: Sep. 11, 2018

(54) SECURITY PREJUDGMENT BASED ON CHARACTERISTIC INFORMATION

(71) Applicant: Alibaba Group Holding Limited, Grand Cayman (KY)

(72) Inventor: Jinhua Wang, Hangzhou (CN)

(73) Assignee: Alibaba Group Holding Limited, Grand Cayman (KY)

(*) Notice: Subject to any disclaimer, the term of this patent is extended or adjusted under 35 U.S.C. 154(b) by 0 days.

(21) Appl. No.: 15/390,019

(22) Filed: Dec. 23, 2016

(65) Prior Publication Data
US 2017/0186298 A1    Jun. 29, 2017

(30) Foreign Application Priority Data

Dec. 25, 2015 (CN) .......................... 2015 1 0994221

(51) Int. Cl.
| | | |
|---|---|---|
| G08B 21/02 | (2006.01) | |
| G08B 21/18 | (2006.01) | |
| G08B 25/10 | (2006.01) | |
| G08B 31/00 | (2006.01) | |
| H04L 29/08 | (2006.01) | |
| H04W 4/14 | (2009.01) | |

(52) U.S. Cl.
CPC .......... *G08B 21/02* (2013.01); *G08B 21/182* (2013.01); *G08B 25/10* (2013.01); *G08B 31/00* (2013.01); *H04L 67/12* (2013.01); *H04W 4/14* (2013.01)

(58) Field of Classification Search
CPC ...... G08B 21/02; G08B 21/182; G08B 25/10; G08B 31/00; H04L 67/12; H04W 4/14
See application file for complete search history.

(56) References Cited

U.S. PATENT DOCUMENTS

| | | | | | |
|---|---|---|---|---|---|
| 4,129,125 | A | * | 12/1978 | Lester | ................. A61B 5/0002 374/142 |
| 2008/0231462 | A1 | | 9/2008 | Hobart | |
| 2011/0090885 | A1 | | 4/2011 | Safavi | |

(Continued)

FOREIGN PATENT DOCUMENTS

KR         101334627        11/2013

OTHER PUBLICATIONS

The PCT Search Report and Written Opinion dated Mar. 13, 2017 for PCT application No. PCT/US16/68525, 12 pages.

*Primary Examiner* — Nader Bolourchi
(74) *Attorney, Agent, or Firm* — Lee & Hayes, PLLC

(57) ABSTRACT

An example method of security prejudgment based on characteristic information include receiving characteristic information of a monitored party from the monitored party, calculating security status information of the monitored party based on a probability of danger that has been stored and corresponds to the characteristic information of the monitored party, determining that the security status information is greater than a first threshold, performing an appropriate operation based on the determination. Accordingly, the technical solution of the present disclosure solves a problem that presetting of monitoring conditions cannot cover potential surrounding risks that result in a safety hazard. Further, the technical solution can monitor risks that are not reflected by spatial information. After identifying and warning based on the characteristic information, potential risks may be avoided before occurring without wasting data traffic.

20 Claims, 10 Drawing Sheets

(56) References Cited

U.S. PATENT DOCUMENTS

| | | |
|---|---|---|
| 2012/0010488 A1 | 1/2012 | Henry et al. |
| 2012/0146789 A1 | 6/2012 | De Luca |
| 2014/0025724 A1 | 1/2014 | Granger et al. |
| 2014/0143064 A1 | 5/2014 | Tran |
| 2014/0237575 A1 | 8/2014 | Geil |
| 2015/0161867 A1 | 6/2015 | Bell et al. |
| 2015/0373521 A1 | 12/2015 | Olesen et al. |
| 2016/0012545 A1 | 1/2016 | Amigo et al. |
| 2016/0019463 A1 | 1/2016 | Bhaskaran |

* cited by examiner

SECURITY PREJUDGMENT BASED ON CHARACTERISTIC INFORMATION

CROSS REFERENCE TO RELATED PATENT APPLICATIONS

This application claims priority to Chinese Patent Application No. 201510994221.X, filed on Dec. 25, 2015, entitled "Method, device, and system of security prejudgment based on characteristic information," which is hereby incorporated by reference in its entirety.

TECHNICAL FIELD

The present disclosure relates to cloud computing technology, and particularly to a method of security prejudgment based on characteristic information, a method of acquiring characteristic information, a system for security prejudgment based on characteristic information, a device for security prejudgment based on characteristic information and an electronic device thereof, and a device for acquiring characteristic information and an electronic device thereof.

BACKGROUND

In daily life, there are hidden dangers relating to factors that affect people's safety or interests with respect to a certain condition, thing, or event. Hidden dangers may cause personal injuries or property damage. Recently, digital applications related to various risks have been widely used. These applications use sophisticated computer networks, GPS, visualization, and database technologies. By tracking or monitoring, such as monitoring children travel electronic fence systems, security risks such as child loss may be prevented. However, a variety of risks is in the existing monitoring systems such that dangerous conditions have to be preset and monitored. Therefore, if potential risks are not identified, people will have to seek help by calling police after an accident occurs.

Thus, since the presetting of dangerous conditions may not cover surrounding dangerous conditions, a safety hazard may occur. Although intuitive and vivid spatial information of visual carriers (e.g., maps) may be used to monitor potential dangerous conditions, certain dangerous conditions not reflected by the spatial information such as maps may not be well monitored. In addition, during monitoring a target, data transmission is normally performed via wireless communications, which results in a waste of traffic for prolonged monitoring processes.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter. The term "technique(s) or technical solution(s)" for instance, may refer to apparatus(s), system(s), method(s) and/or computer-readable instructions as permitted by the context above and throughout the present disclosure.

Implementations of the present disclosure relate to a method of security prejudgment based on characteristic information, a method of acquiring characteristic information, and a system for security prejudgment based on characteristic information to solve problems under the conventional techniques. Implementations further relate to a device for security prejudgment based on characteristic information and an electronic device thereof, and a device for acquiring characteristic information and an electronic device thereof.

Implementations of the present disclosure relate to a method of security prejudgment based on the characteristic information. The method includes receiving characteristic information of a monitored party from the monitored party, calculating security status information of the monitored party based on a probability of danger that has been stored and corresponds to the characteristic information of the monitored party, determining whether the security status information is greater than a first threshold, and performing an appropriate operation based on the determination.

In implementations, the computing device may calculate the security status information of the monitored party based on the probability of danger that has been stored and corresponds to the characteristic information of the monitored party by calculating the security status information of the monitored party based on Bayes' theorem using a probability of danger that has been stored and corresponds to the characteristic information of the monitored party.

In implementations, the appropriate operation based on the determination may be performed in the following manners. If the security status information is greater than a first threshold, a computing device (e.g., a computing device associated with a monitored party or a monitoring party) may transmit to a predetermined monitoring party a login key used for acquiring the characteristic information of the monitored party. If the security status information is not greater than a first threshold, the computing device may transmit a prompt message generated based on characteristic information of the monitoring party to the monitored party.

In implementations, the computing device may transmit to the predetermined monitoring party the login key used for acquiring the characteristic information of the monitored party by transmitting to the predetermined monitoring party the login key used for acquiring the characteristic information of the monitored party via an SMS text message.

In implementations, after transmitting to the predetermined monitoring party the login key used for acquiring the characteristic information of the monitored party, the computing device may transmit an instruction to the monitored party to set a predetermined time interval for acquiring characteristic information as real-time access.

In implementations, prior to the transmitting the prompt message generated based on the characteristic information of the monitored party to the monitored party, the computing device may determine whether the security status information is greater than a second threshold. If the security status information is greater than a second threshold, the computing device may transmit the prompt message generated based on the characteristic information of the monitored party to the monitored party. If the security status information is not greater than a second threshold, the computing device may transmit an instruction to the monitored party to extend a predetermined time interval for acquiring characteristic information.

In implementations, after receiving the characteristic information of a monitored party from the monitored party, the computing device may receive alarm information from the monitored party, and trigger and perform the operation of transmitting to the predetermined monitoring party the login key used for acquiring the characteristic information of the monitored party.

In implementations, the monitored party is a mobile terminal, and the characteristic information of the monitored party may include at least one of current location information, current time information, movement status information, gender, and age.

In implementations, the computing device may calculate the security status information of the monitored party based on Bayes' theorem using a probability of danger that has been stored and corresponds to the characteristic information of the monitored party. For example, the computing device may acquire predetermined probabilities of danger corresponding to the current location information, the current time information, the movement status information, the gender, and the age in the characteristic information of the monitored party, and introduce a probability of danger of the current location information, a probability of danger of the current time information, a probability of danger of the movement status information, a probability of danger of the gender, and a probability of danger of the age into the Bayes' theorem to calculate the probability of danger to the monitored party, and designate the probability of danger to the monitored party as the security status information of the monitored party.

In implementations, the computing device may calculate the security status information of the monitored party based on the probability of danger that has been stored and corresponds to the characteristic information of the monitored party by mapping the current location information in the characteristic information of the monitored party to the resident location information of the monitored party. If the current location information is not within a predetermined range of the resident location information of the monitored party, the computing device may start a timer. If the current location information is within a predetermined range of the resident location information of the monitored party, the computing device may terminate the timer.

In response to a determination that a time period recorded by the timer is greater than a predetermined time period, the computing device may generate the probability of danger to the monitored party that is greater than the first threshold and designate the probability of danger to the monitored party as the security status information of the monitored party.

In implementations, after transmitting to the predetermined monitoring party the login key used for acquiring the characteristic information of the monitored party, the computing device may record the current location information in the characteristic information of the monitored party, and designate the current location information as a trigger location information. For example, each received current location information in the characteristic information of the monitored party is projected onto a projection coordinate.

In implementations, the alarm information that is sent by the monitored party may include at least one of current location information, current time information, or movement status information.

In implementations, the monitored party may include a smart device capable of monitoring health information, the characteristic information of the monitored party may include at least one of a gender, an age, a heart rate, a body temperature, or a respiration rate.

In implementations, the computing device may calculate the security status information of the monitored party based on Bayes' theorem using a probability of danger that has been stored and corresponds to the characteristic information of the monitored party by acquiring predetermined probabilities of danger corresponding to the gender, the age, the heart rate, the body temperature and the respiration rate in the characteristic information of the monitored party, introducing a probability of danger of the gender, a probability of danger of the age, a probability of danger of the heart rate, a probability of danger of the body temperature, and a probability of danger of the respiration rate into the Bayes' theorem to calculate the probability of danger to the monitored party, and designating the probability of danger to the monitored party as the security status information of the monitored party.

In implementations, with respect to receiving the characteristic information of a monitored party from the monitored party, the characteristic information of the monitored party may further include longitudinal acceleration. The computing device may calculate the security status information of the monitored party based on the probability of danger that has been stored and corresponds to the characteristic information of the monitored party further by acquiring a probability of danger corresponding to the longitudinal acceleration in the characteristic information of the monitored party.

In implementations, the alarm information that is sent by the monitored party may include at least one of a heart rate, a body temperature, or a respiratory rate.

In implementations, the monitored party may include a sensor device capable of detecting a physical parameter, and the characteristic information of the monitored party may include at least one of a temperature, brightness, a volume or a gas concentration.

In implementations, the computing device may calculate the security status information of the monitored party based on Bayes' theorem using a probability of danger that has been stored and corresponds to the characteristic information of the monitored party by acquiring predetermined probabilities of danger corresponding to the temperature, the brightness, the volume, the gas concentration in the characteristic information of the monitored party, introducing a probability of danger of the temperature, a probability of danger of the brightness, a probability of danger of the volume, and a probability of danger of the gas concentration into the Bayes' theorem to calculate the probability of danger to the monitored party, and designating the probability of danger to the monitored party as the security status information of the monitored party.

In implementations, the alarm information that is sent by the monitored party may include at least one of a temperature, brightness, a volume or a gas concentration.

Accordingly, implementations of the present disclosure relate to a device of security prejudgment based on the characteristic information. The device may include a characteristic information receiving module configured to receive characteristic information of a monitored party from the monitored party, a security state information calculation module configured to calculate security status information of the monitored party based on a probability of danger that has been stored and corresponds to the characteristic information of the monitored party, a security state information judgment module configured to determine that the security status information is greater than a first threshold, and an execution module configured to perform an appropriate operation based on the determination.

In implementations, the security state information calculation module may be configured to calculate the security status information of the monitored party based on Bayes' theorem using a probability of danger that has been stored and corresponds to the characteristic information of the monitored party.

In implementations, the execution module may include a login key sending sub-module configured to receive a determining result from a first threshold judgment sub-module. If the security status information is greater than a first threshold, the computing device may transmit to a predetermined monitoring party a login key used for acquiring the characteristic information of the monitored party, and a prompt message sending sub-module configured to configured to receive a determining result from a first threshold judgment sub-module; if the security status information is not greater than a first threshold, the computing device may transmit a prompt message generated based on characteristic information of the monitoring party to the monitored party.

In implementations, the login key sending sub-module may be configured to transmit to the predetermined monitoring party the login key used for acquiring the characteristic information of the monitored party via an SMS text message.

In implementations, the execution module may include a real-time command sending sub-module configured to transmit to the predetermined monitoring party the login key used for acquiring the characteristic information of the monitored party, and then transmit an instruction to the monitored party to set a predetermined time interval for acquiring characteristic information as real-time access.

In implementations, the execution module may include a second threshold judgment sub-module configured to transmitting the prompt message generated based on the characteristic information of the monitored party to the monitored party after determining that the security status information is greater than a second threshold, a message triggering sub-module configured to receive a determining result from the second threshold judgment sub-module and to trigger the prompt message sending sub-module if the determining result is positive, and an extension instruction sending sub-module configured to receive a determining result from the second threshold judgment sub-module and to transmit an instruction to the monitored party to extend a predetermined time interval for acquiring characteristic information if the determining result is negative.

In implementations, the device may further include an alarm information receiving module configured to receive alarm information from the monitored party, and a login key sending sub-module triggering module configured to trigger the login key sending sub-module.

In implementations, the characteristic information receiving module may be configured to receive the characteristic information of the monitored party including at least one of current location information, current time information, movement status information, a gender, or an age if the monitored party is a mobile terminal.

In implementations, the security state information calculation module may include a danger probability acquisition sub-module configured to acquire predetermined probabilities of danger corresponding to the current location information, the current time information, the movement status information, the gender, and the age in the characteristic information of the monitored party, a probability calculation sub-module configured to introduce a probability of danger of the current location information, a probability of danger of the current time information, a probability of danger of the movement status information, a probability of danger of the gender, and a probability of danger of the age into the Bayes' theorem and to calculate the probability of danger to the monitored party, and a security state information generation sub-module configured to designate the probability of danger to the monitored party as the security status information of the monitored party.

In implementations, the security state information calculation module may include a matching sub-module configured to map the current location information in the characteristic information of the monitored party to the resident location information of the monitored party, a timer starting sub-module configured to start a timer if the current location information is not within a predetermined range of the resident location information of the monitored party, a timer termination sub-module configured to terminate the timer if the current location information is within a predetermined range of the resident location information of the monitored party, and a first probability generating sub-module configured to, in response to a determination that a time period recorded by the timer is greater than a predetermined time period, and the computing device may generate the probability of danger to the monitored party that is greater than the first threshold and designate the probability of danger to the monitored party as the security status information of the monitored party.

In implementations, the execution module may further include a location information recording sub-module configured to transmit to the predetermined monitoring party the login key used for acquiring the characteristic information of the monitored party, record the current location information in the characteristic information of the monitored party, and designate the current location information as a trigger location information, and a coordinate system projection sub-module configured to project each received current location information in the characteristic information of the monitored party onto a projection coordinate.

In implementations, the device may further include an alarm information receiving module configured to receive alarm information from the monitored party, which may include at least one of current location information, current time information, movement status information, a gender, or an age.

In some implementations, the characteristic information receiving module may be configured to receive the characteristic information of the monitored party including at least one of a gender, an age, a heart rate, a body temperature, or a respiration rate.

In implementations, the security state information calculation module may further include a danger probability acquisition sub-module configured to acquire predetermined probabilities of danger corresponding to the gender, the age, the heart rate, the body temperature and the respiration rate in the characteristic information of the monitored party, a probability calculation sub-module configured to introduce a probability of danger of the gender, a probability of danger of the age, a probability of danger of the heart rate, a probability of danger of the body temperature, and a probability of danger of the respiration rate into the Bayes' theorem and calculate the probability of danger to the monitored party, and a security state information generation sub-module configured to designate the probability of danger to the monitored party as the security status information of the monitored party.

In implementations, the characteristic information receiving module may be configured to further receive longitudinal acceleration. The security state information calculation module may include a longitudinal acceleration risk probability acquisition sub-module configured to acquire a probability of danger corresponding to the longitudinal acceleration in the characteristic information of the monitored party.

In implementations, the device may further include an alarm information receiving module configured to receive alarm information from the monitored party, which may include at least one of a heart rate, a body temperature, or a respiratory rate.

In implementations, the monitored party may include a sensor device capable of detecting a physical parameter. For example, the characteristic information receiving module may be configured to receive the characteristic information of the monitored party including at least one of a temperature, brightness, a volume or a gas concentration.

In implementations, the security state information calculation module may include a danger probability acquisition sub-module configured to acquire predetermined probabilities of danger corresponding to the temperature, the brightness, the volume, the gas concentration in the characteristic information of the monitored party, a probability calculation sub-module configured to introduce a probability of danger of the temperature, a probability of danger of the brightness, a probability of danger of the volume, and a probability of danger of the gas concentration into the Bayes' theorem and calculate the probability of danger to the monitored party, a security state information generation sub-module configured to designate the probability of danger to the monitored party as the security status information of the monitored party.

In implementations, the device may further include an alarm information receiving module configured to receive alarm information from the monitored party, which may include at least one of: a temperature, brightness, a volume or a gas concentration.

In addition, the implementations further relate to an electronic device. the electronic device may include a display, one or more processors, and memory configured to store a characteristic information prejudgment program, executed by the one or more processors to: receive characteristic information of a monitored party from the monitored party, calculate security status information of the monitored party based on a probability of danger that has been stored and corresponds to the characteristic information of the monitored party, determine that the security status information is greater than a first threshold, and perform an appropriate operation based on the determination.

In addition, implementations of the present disclosure relate to a method of acquiring characteristic information. The method may include acquiring the characteristic information of a monitored party based on a predetermined time interval, transmitting the characteristic information of the monitoring party to a server terminal, receiving an instruction to the monitored party to set a predetermined time interval for acquiring characteristic information as real-time access or an instruction to the monitored party to extend a predetermined time interval for acquiring characteristic information, and changing the time interval based on the acquired characteristic information of the monitoring party.

In implementations, the monitored party is a mobile terminal, and the characteristic information of the monitored party that is acquired based on the predetermined time interval may include at least current location information, current time information, and movement status information.

In implementations, prior to the acquiring the characteristic information of a monitored party based on a predetermined time interval, the computing device may receive input of a gender, an age, and resident location information on the monitoring party.

In implementations, after transmitting the characteristic information of the monitoring party to the server terminal, the computing device may receive a touch operation on an alarm area of the display and a three-strike operation on a power button, acquire the characteristic information of the monitoring party, and transmit alarm information to the server terminal. The alarm information may include the characteristic information of the monitoring party. For example, the alarm area may include an alarm area of a screen locking interface, or an alarm area of a desktop In implementations, with respect to the transmitting the alarm information to the server terminal, the computing device may transmit contact information to the monitored party and the alarm information to a map application.

In implementations, the monitored party may include a smart device capable of monitoring health information, and the characteristic information of the monitored party that is acquired based on the predetermined time interval may include at least a heart rate, a body temperature, a respiratory rate and longitudinal acceleration.

In implementations, prior to the acquiring the characteristic information of a monitored party based on a predetermined time interval, the computing device may receive input of a gender and an age on the monitoring party.

In implementations, after transmitting the characteristic information of the monitoring party to the server terminal, the computing device may receive a touch operation on an alarm area of the display and a two-strike operation on a power button, acquire the characteristic information of the monitoring party, and transmit alarm information to the server terminal. The alarm information may include the characteristic information of the monitoring party. For example, the alarm area may include an alarm area of a screen locking interface, or an alarm area of a desktop.

In implementations, the monitored party may include a sensor device capable of detecting a physical parameter, and the characteristic information of the monitored party that is acquired based on the predetermined time interval may include at least one of a temperature, brightness, a volume or a gas concentration.

In implementations, after transmitting the characteristic information of the monitoring party to the server terminal, the computing device may receive a prompt message generated based on characteristic information of the monitoring party to from the server terminal.

Accordingly, implementations of the present disclosure relate to a device for acquiring characteristic information. The device may include a characteristic information acquiring module configured to acquire the characteristic information of a monitored party based on a predetermined time interval, a characteristic information transmitting module configured to transmit the characteristic information of the monitoring party to a server terminal, a receiving instruction module configured to receive an instruction to the monitored party to set a predetermined time interval for acquiring characteristic information as real-time access or an instruction to the monitored party to extend a predetermined time interval for acquiring characteristic information, and a time interval modification module configured to change the time interval based on the acquired characteristic information of the monitoring party.

In implementations, the characteristic information acquiring module may be configured to acquire current location information, current time information, and movement status information of the monitoring party based on the predetermined time interval if the monitored party is a mobile terminal.

In implementations, the device may further include an information receiving module configured to acquiring the characteristic information of the monitored party based on the predetermined time interval, and to receive input of a gender, an age, and resident location information on the monitoring party.

In implementations, the device may further include a touch operation receiving module configured to receive a touch operation on an alarm area of the display and a three-strike operation on a power button after transmitting the characteristic information of the monitoring party to a server terminal. The alarm area may include an alarm area of a screen locking interface, or an alarm area of a desktop. The device may further include a current characteristic information obtaining module configured to acquire the characteristic information of the monitoring party, and an alarm information transmission module configured to transmit the alarm information to the server terminal. For example, the alarm information may include the characteristic information of the monitoring party.

In implementations, the device may further include a third-party transmission module configured to transmit contact information to the monitored party and the alarm information to a map application.

In implementations, the characteristic information acquiring module may be configured to acquire a heart rate, a body temperature, a respiratory rate and longitudinal acceleration of the monitoring party based on a predetermined time interval if the monitored party includes a smart device capable of monitoring health information.

In implementations, the device may further include an information receiving module configured to acquire the characteristic information of the monitored party based on the predetermined time interval, and receive input of a gender and an age on the monitoring party.

In implementations, the device may further include a touch operation receiving module configured to receive a touch operation on an alarm area of the display and a two-strike operation on a power button after transmitting the characteristic information of the monitoring party to a server terminal. The alarm area may include an alarm area of a screen locking interface, or an alarm area of a desktop. The device may further include a current characteristic information obtaining module configured to acquire the characteristic information of the monitoring party, and an alarm information transmission module configured to transmit the alarm information to the server terminal. The alarm information may include the characteristic information of the monitoring party.

In implementations, the characteristic information acquiring module may be configured to acquire a temperature, brightness, a volume, or a gas concentration of the monitoring party based on a predetermined time interval if the monitored party includes a sensor device capable of detecting a physical parameter.

In some implementations, the device may further include a message receiving module configured to receive a prompt message generated based on characteristic information of the monitoring party to from a server terminal after transmitting the characteristic information of the monitoring party to the server terminal.

In addition, the implementations further relate to an electronic device. the electronic device may include a display, one or more processors, and memory configured to store a characteristic information acquiring program, executed by the one or more processors to: acquire characteristic information of a monitored party based on a predetermined time interval, transmit the characteristic information of the monitoring party to a server terminal, receive an instruction to the monitored party to set a predetermined time interval for acquiring characteristic information as real-time access or an instruction to the monitored party to extend a predetermined time interval for acquiring characteristic information, and change the time interval based on the acquired characteristic information of the monitoring party.

In addition, implementations of the present disclosure relate to a system for security prejudgment based on the characteristic information. The system may include any device of security prejudgment based on characteristic information as described above, and any device for acquiring characteristic information as described above.

Compared with the conventional techniques, implementations of the present disclosure have the following advantages.

The implementations of the present disclosure relate to a method of security prejudgment and a device as well as an electronic device thereof. The implementations include receiving characteristic information of a monitored party from the monitored party, calculating security status information of the monitored party based on a probability of danger that has been stored and corresponds to the characteristic information of the monitored party, determining that the security status information is greater than a first threshold, and performing an appropriate operation based on the determination. The technical solution of the present disclosure solves a problem that preset monitoring conditions cannot cover potential surrounding risks that result in a safety hazard. Further, the technical solution can monitor risks that are not reflected by spatial information. By identifying and pre-warning the characteristic information, potential risks may be avoided before occurring, improving personal safety and protecting property.

Implementations of the present disclosure relate to methods and devices for acquiring characteristic information. The method may include acquiring the characteristic information of a monitored party based on a predetermined time interval, transmitting the characteristic information of the monitoring party to a server terminal, receiving an instruction to the monitored party to set a predetermined time interval for acquiring characteristic information as real-time access or an instruction to the monitored party to extend a predetermined time interval for acquiring characteristic information, and changing the time interval based on the acquired characteristic information of the monitoring party. The technical solution solves the problem of data traffic waste caused by wireless data communication and transmission when monitoring a target for a long time.

BRIEF DESCRIPTION OF THE DRAWINGS

The detailed description is described with reference to the accompanying figures. Obviously, the described figures are merely a part of implementations of the present disclosure. Those skilled in the art should understand that other figures may be obtained in accordance with the implementations of the present disclosure.

DETAILED DESCRIPTION

The detailed description is described with reference to the accompanying figures. Below in conjunction with the accompanying drawings the implementations of the present disclosure are described. It should be noted that, without conflict, implementations and the features thereof may be combined in various ways.

In the following description, numerous specific details are set forth in order to fully understand the present disclosure. However, this application can be in many other ways than those described herein. Those skilled in the art can make similar promotion without departing from the present disclosure connotation case. Accordingly, this application is therefore not limited to the specific embodiments disclosed below.

The present disclosure relates to a method of security prejudgment based on characteristic information, a method of acquiring characteristic information, a system for security prejudgment based on characteristic information, a device for security prejudgment based on characteristic information and an electronic device thereof, and a device for acquiring characteristic information and an electronic device thereof. Below are provided detailed implementations.

At present digital applications associated with various risks have been widely used. These applications use a sophisticated computer network, GPS, visualization, database technologies. By tracking or monitoring, such as monitoring children travel electronic fence system, security risks such as child loss may be prevented. However, a variety of risks is in the existing monitoring systems. For example, dangerous conditions have to be set and monitored, and therefore potential risks may not be identified. People may seek help by calling police after an accident occurs. Thus, since the preset dangerous conditions may not cover surrounding dangers/risks, a safety hazard may occur. Although intuitive and vivid spatial information of visual carriers (e.g., maps) may be used to monitor potential dangerous conditions, certain dangerous conditions not reflected by the maps may not be well monitored. In addition, while monitoring a target, data transmission is normally performed via wireless communications, which result in a waste of traffic for prolonged monitoring. To solve this problem, the implementations of the present disclosure include receiving characteristic information of a monitored party from the monitored party, calculating security status information of the monitored party based on a probability of danger that has been stored and corresponds to the characteristic information of the monitored party, determining that the security status information is greater than a first threshold, and performing an appropriate operation based on the determination to achieve the security prejudgment.

Implementations of the present disclosure relate to a method of security prejudgment based on the characteristic information. The method may include the following operations.

Figure 1:
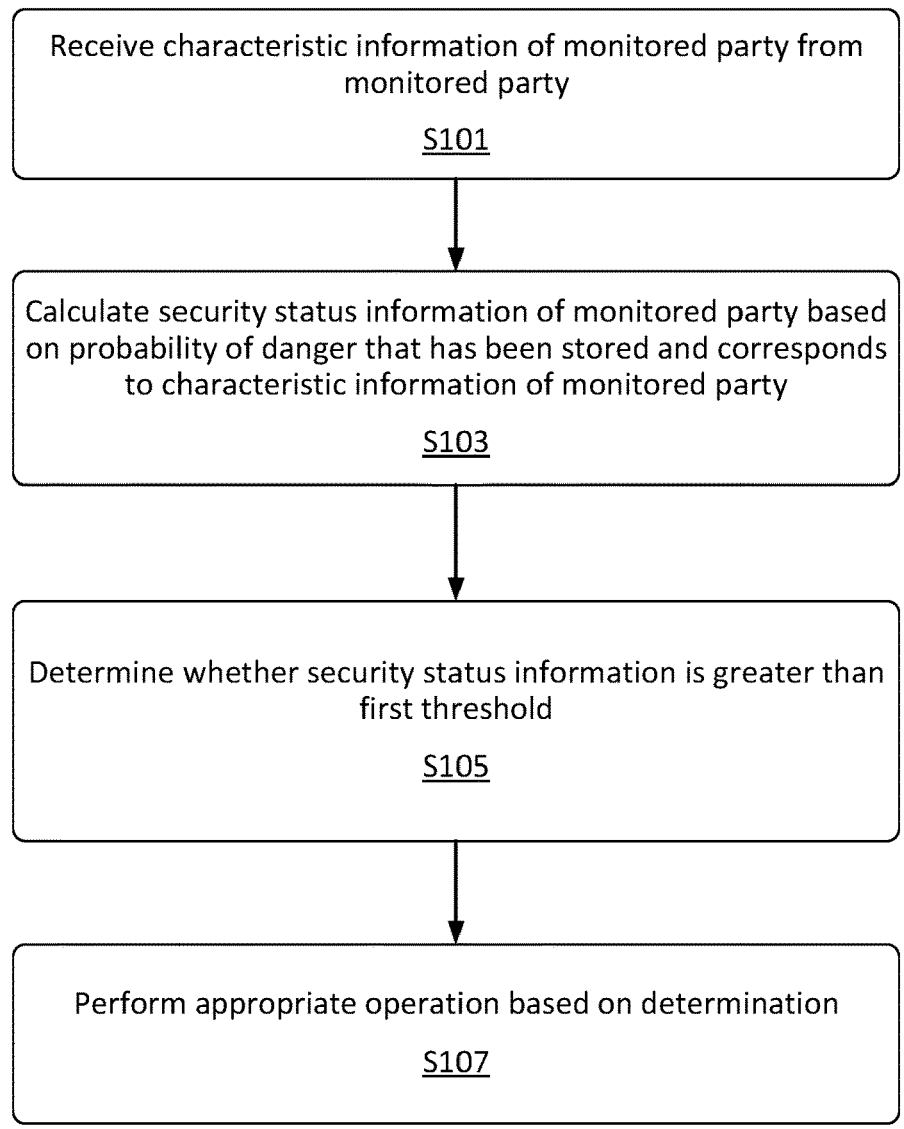
FIG. 1 is a flowchart illustrating a method of security prejudgment based on characteristic information in accordance with the implementations of the present disclosure.

FIG. 1 is a flowchart illustrating a method of security prejudgment based on characteristic information in accordance with the implementations of the present disclosure.

At S101, a computing device may receive characteristic information of a monitored party from the monitored party.

In implementations, the computing device may receive characteristic information of a monitored party from the monitored party in the following manners. GPRS\3G\4G or WIFI connection may be established with the monitored party. The computing device may receive characteristic information of a monitored party from the monitored party.

At S103, the computing device may calculate security status information of the monitored party based on a probability of danger that has been stored and corresponds to the characteristic information of the monitored party.

At S101, the computing device may receive the characteristic information of a monitored party from the monitored party, and acquire security status information of the monitored party.

In implementations, the calculating the security status information of the monitored party based on the probability of danger that has been stored and corresponds to the characteristic information of the monitored party may be performed in the following manners: calculating the security status information of the monitored party based on Bayes' theorem using a probability of danger that has been stored and corresponds to the characteristic information of the monitored party.

It is understood that the computing device may calculate the security status information of the monitored party based on Bayes' theorem using a probability of danger that has been stored and corresponds to the characteristic information of the monitored party. The computing device may calculate security status of the monitored party in the above-described condition based on a danger probability of each detailed parameters of the characteristic information. In some implementations, the security status information of the monitored party refers to the probability of danger of the monitored party.

It should be noted that Bayes' theorem proposed by the British mathematician (Thomas Bayes) describes a probability between two conditions, for example, $P(A|B)$ and $P(B|A)$. In accordance with the multiplication rule, $P(A \cap B) = P(A)*P(B|A) = P(B)*P(A|B)$ can be exported immediately. The above formula can also be transformed into: $P(B|A) = P(A|B)*P(B)/P(A)$. Bayes' theorem can provide approximate results for search data and be used to determine the relationship between symptoms and diseases.

For example, the characteristic information of the monitored party includes a current time and a driving speed. If an accident at the current time is represented using event A and an accident at the current speed is represented using event B, an accident probability of event A is $P(A)=8/20$, and an accident probability of event B is $P(B)=1/2$, $P(B|A)=7/10$.

According to Bayes' theorem, there are: P(A|B)=(7/10)*(1/2)/(8/20)=0.875, which indicates the accident probability at the current time and the current driving speed is 0.875.

At S105, the computing device may determine whether the security status information is greater than a first threshold.

At S103, the computing device may calculate the security status information of the monitored party, and perform the security prejudgment based on the security status information of the monitored party.

In implementations, the security status information of the monitored party refers to the probability of danger to the monitored party, which is a preset first threshold of danger probabilities. The determination that the security status information of the monitored party is greater than the first threshold may be performed in the following manners. The computing device may determine whether the probability of danger to the monitored party is greater than a predetermined probability of danger. For example, the first threshold is 0.7.

It should be noted that the first threshold value is set to identify the received characteristic information from each latitude, and the computing device may determine that the monitored party is in a high danger status.

At S107, the computing device may perform an appropriate operation based on the determination.

At S105, the computing device may receive the determining result of the monitored party, and make the appropriate processing operations based on the determining result.

Figure 2:
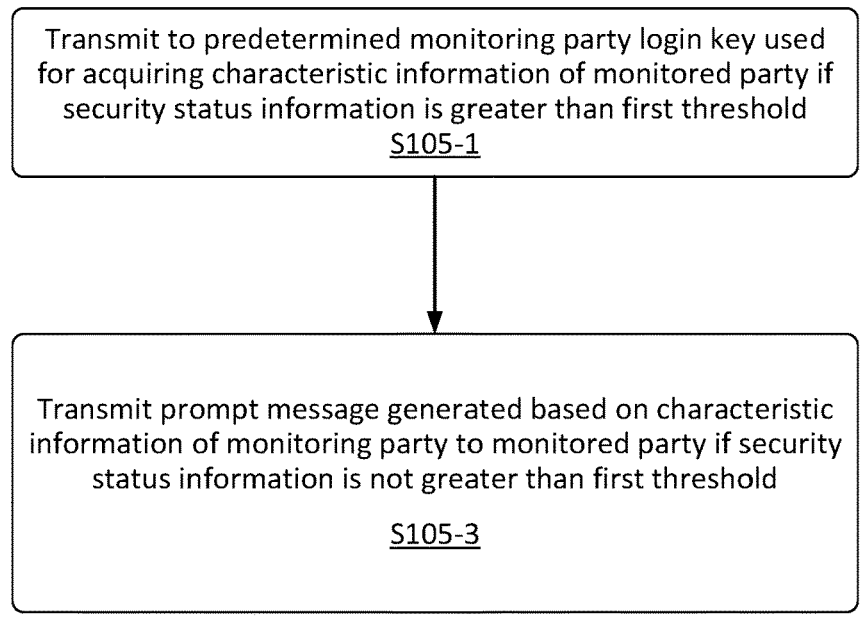
FIG. 2 is a flowchart illustrating a process of performing operations based on a determining result on in accordance with the implementations of the present disclosure.

In implementations, the appropriate operation may be performed based on the determination, as described in details in S105-1 to S105-3 in FIG. 2.

FIG. 2 is a flowchart illustrating a process of performing operations based on a determining result on in accordance with the implementations of the present disclosure.

At S105-1, the computing device may transmit to a predetermined monitoring party a login key used for acquiring the characteristic information of the monitored party if the security status information is greater than a first threshold.

If the probability of danger to the monitored party is not less than a predetermined probability of danger, the computing device may perform the operation of the transmitting to the predetermined monitoring party the login key used for acquiring the characteristic information of the monitored party. The computing device may transmit to the predetermined monitoring party the login key used for acquiring the characteristic information of the monitored party may be performed in the following manners. The computing device may transmit to the predetermined monitoring party the login key used for acquiring the characteristic information of the monitored party via a Short Messaging Service (SMS) text message.

It should be noted that SMS is the first short message service, and is now one of the highest penetration rates of short message services. Currently, the length of such a short message is limited to 140 bytes, and these bytes can be text. SMS text messaging is simple and easy to be used, and therefore widely used by the public. But SMS belongs to the first generation of wireless data services, which is limited in technical standards with respect to content and applications. SMS text messaging is also a store and forward service. In other words, the message is not sent directly from sender to receiver, but forwarded through SMS centers. If the receiver is not an unconnected state (e.g., probably the phone is turned off), the message will be resent.

It should be noted that the monitoring party is a predetermined terminal associated with the server terminal that is connected with the monitored party. The monitoring party may receive the characteristic information of the monitored party via the server terminal, and monitor visualization may be generated on the server terminal based on the characteristic information of the monitored party after login using the login key. For example, if the monitored party corresponds to a student, the monitoring party corresponds to parents of the student. The monitoring party may log in the server terminal and watch the trajectory of the monitored party that is generated by the server terminal based on the characteristic information.

In this embodiment, the login Key includes: account information of the monitoring party, a timestamp associated with the login using the login key, and a verification code generated when the monitoring party logs using the login key. The verification code refers to a set of random numbers when generating the login key. The verification code may include other forms, including any possible way in the conventional techniques and other forms of the development of new techniques. This will not be limited.

If the monitored party is in a highly dangerous condition (e.g., the danger probability is greater than a first threshold), the server terminal may transmit the login key to a corresponding monitoring party, which has been connected to the monitored party, for example, in response to an urgent demand in some unforeseen circumstances rather than long-term needs. Thus, the login key may be a temporary login key, which may be used only once (e.g., single sign-key). That is, the monitoring party may log in the server terminal and watch the visualization of the monitored party that is generated by the server terminal based on the characteristic information, and then the login key will be expired.

To accurate the visualization, after transmitting to the predetermined monitoring party the login key used for acquiring the characteristic information of the monitored party, the server terminal may transmit an instruction to the monitored party to set a predetermined time interval for acquiring characteristic information as real-time access. For example, the predetermined time interval may be reset as 1 second.

At S105-3, the computing device may transmit a prompt message generated based on characteristic information of the monitoring party to the monitored party if the security status information is not greater than a first threshold.

If the probability of danger to the monitored party is less than a predetermined probability of danger, the computing device may transmit the prompt message generated based on the characteristic information of the monitored party to the monitored party. The computing device may transmit a prompt message generated based on characteristic information of the monitoring party to the monitored party in the following manners. The computing device may generate the security status information of the monitored party based on the characteristic information of the monitored party, and transmit the message corresponding to the security status information. For example, the prompt message may gradually increase the intensity of the message content based on the gradient of the security status information from small to large. If the security status information of the monitored party is "0", the message content includes the prompt message indicating being safe. If the security status information is "0.6", the message content includes the prompt message that is not safe, and the prompt message may recommend going home as soon as possible.

When the security status information is in a moderate danger, the computing may perform the following operations to make the prompt message generated based on the characteristic information of the monitored party more accurate. Prior to the transmitting the prompt message generated based on the characteristic information of the monitored party to the monitored party, the present disclosure provides a preferred implementation. In some implementations, operations S104-S104-5 may be performed.

Figure 3:
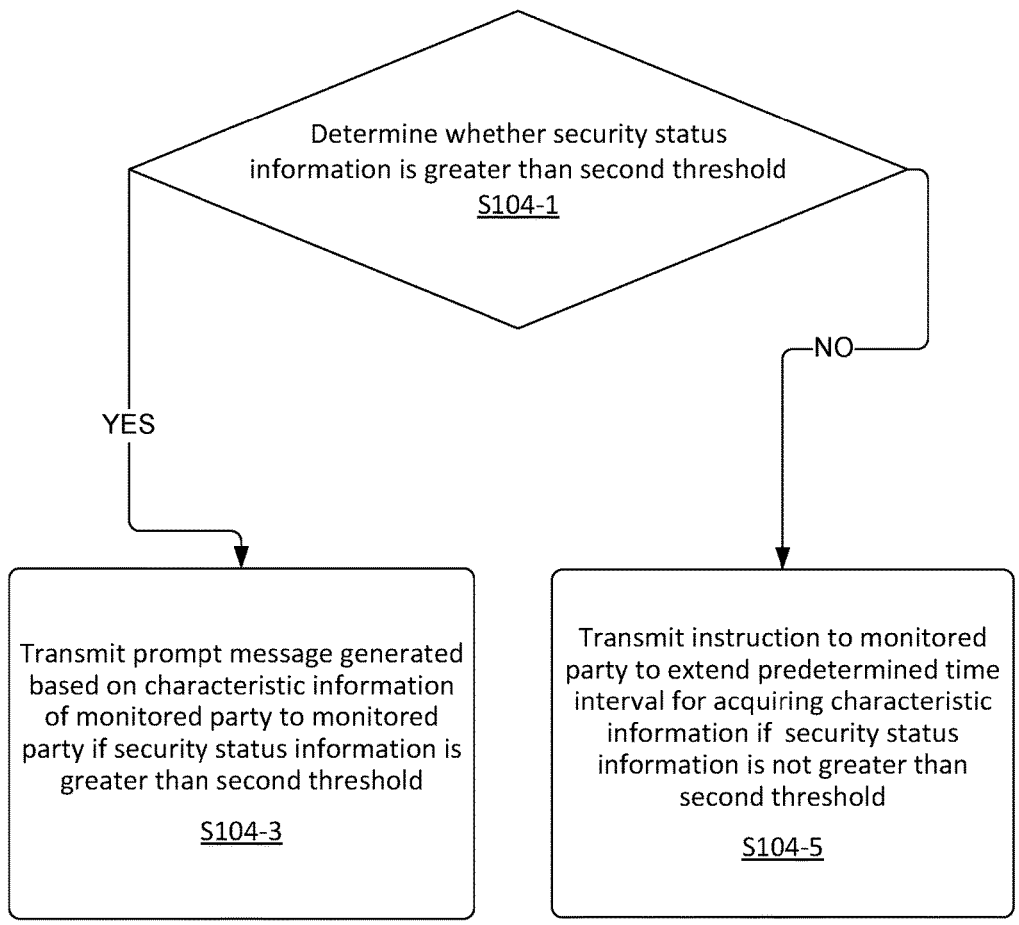
FIG. 3 is a flowchart illustrating a process of determining whether security status information is greater than a second threshold in accordance with the implementations of the present disclosure.

FIG. 3 is a flowchart illustrating a process of determining whether security status information is greater than a second threshold in accordance with the implementations of the present disclosure.

At S104-1, the computing device may determine whether the security status information is greater than a second threshold.

In implementations, the security status information of the monitored party refers to the probability of danger to the monitored party, which is a preset first threshold of danger probabilities. The determination that the security status information of the monitored party is greater than the second threshold may be performed in the following manners. The computing device may determine whether the probability of danger to the monitored party is greater than the second probability of danger. For example, the first threshold is "0.4".

It should be noted that the second threshold value is set to identify the received characteristic information from each latitude, and the computing device may determine that the monitored party is in a high danger status.

At S104-3, the computing device may transmit the prompt message generated based on the characteristic information of the monitored party to the monitored party if the monitored party is in a high danger status. For example, the security status information is greater than a second threshold.

If the probability of danger to the monitored party is greater than the second probability of danger, the computing device may transmit the prompt message generated based on the characteristic information of the monitored party to the monitored party.

For example, the prompt message gradually increases the intensity of the message content based on the gradient of the security status information from small to large. If the security status information is "0.4", the message content includes the prompt message that is moderately safe, and the prompt message may recommend going home as soon as possible. If the security status information is "0.6", the message content includes the prompt message that is not safe, and the prompt message may recommend going home as soon as possible.

At S104-5, the computing device may transmit an instruction to the monitored party to extend a predetermined time interval for acquiring characteristic information if the monitored party is not in a high danger status. For example, the security status information is not greater than a second threshold.

The computing device may transmit an instruction to the monitored party to extend a predetermined time interval for acquiring characteristic information in the following manners. The computing device may generate the security status information of the monitored party based on the characteristic information of the monitored party, and transmit an instruction to the monitored party to extend a predetermined time interval for acquiring characteristic information. For example, the predetermined time interval for acquiring characteristic information is 60 seconds. The instructions of the predetermined time interval for acquiring characteristic information gradually extended the predetermined time interval for acquiring characteristic information based on the gradient of the security status information from small to large. If the security status information is "3", the computing device may extend the time interval for acquiring characteristic information to 30 seconds. If the security status information of the monitored party is "0", the computing device may extend the time interval for acquiring characteristic information to 5 minutes.

In these instances, the computing device may estimate the security status information of the monitored party based on the received characteristic information of the monitored party, and transmit to a predetermined monitoring party a login key used for acquiring the characteristic information of the monitored party. In some implementations, in addition to identifying the security status information of the monitored party based on the characteristic information, the computer device may trigger and perform the operation of the transmitting to the predetermined monitoring party the login key used for acquiring the characteristic information of the monitored party. Detailed information of the connection is provided as follow.

After receiving the characteristic information of a monitored party from the monitored party, the computing device may trigger and perform the operation of the transmitting to the predetermined monitoring party the login key used for acquiring the characteristic information of the monitored party.

It should be noted that the alarm information transmitted to the monitored party includes the characteristic information of the monitored party.

Implementations of the present disclosure relate to a method of security prejudgment based on the characteristic information. The implementations of the method for security prejudgment based on the characteristic information. The computing device may configure types of the monitored parties and receive different types of the characteristic information corresponding to the different types of monitored parties to achieve various types of security prejudgment based on the characteristic information. Implementations of a method of security prejudgment based on the characteristic information may be described using common types of security prejudgment based on various types of characteristic information and various types of the monitored parties. The method of security prejudgment based on characteristic information may include performing security prejudgment on mobile terminals, smart devices, and sensor devices capable of detecting health information. In some implementations, reasonable selection of characteristic information and performing of security prejudgment based on characteristic information on various devices cannot be fully explained and exemplified.

If the monitored party is a mobile terminal, the method of security prejudgment based on characteristic information may be implemented using the following manners.

It should be noted that the implementations may include a method of monitoring between mobile terminals if the monitored party is a mobile terminal. In other words, a monitoring terminal monitors a monitored terminal. The monitored terminal is a terminal that acquires the characteristic information of the monitored terminal and transmits the characteristic information to a server terminal. Therefore, the monitored terminal refers to a monitored party. The monitoring device is a terminal that monitors visualization generated on the server terminal based on the characteristic information of the monitored party after login using the login key. Therefore, the monitoring terminal refers to a monitoring party. It is understood that, in various scenarios, a monitoring party can be the monitoring party and the monitored party. Similarly, a monitored party can be the monitoring party and the monitored party, as described in more detailed below.

At S101, the computing device may receive characteristic information of a monitored party from the monitored party, through GPRS\3G\4G or WIFI connection may be established with the monitored party, acquiring predetermined probabilities of danger corresponding to the current location information, the current time information, the movement status information, the gender, and the age in the characteristic information of the monitored party.

It should be noted that the current location information of the monitored party may include latitude and longitude information of the monitored party or a coding string of geohash of a location (a type of address coding). In some implementations, the location information may be determined using landmarks such as concrete buildings. The current time information includes the system time of the monitored party when the current location information of the monitored party is acquired. Movement information of the monitored party includes lateral acceleration and longitudinal acceleration that are generated during motion changes. The gender and age refer to the gender and age input by a user associated with the monitored party when the user uses the mobile terminal at the first time.

At S103, the computer may calculate security status information of the monitored party based on a probability of danger that has been stored and corresponds to the characteristic information of the monitored party by calculating the security status information of the monitored party based on Bayes' theorem using a probability of danger that has been stored and corresponds to the characteristic information of the monitored party. Detailed operations are provided as follow.

The computing device may acquire predetermined probabilities of danger corresponding to the current location information, the current time information, the movement status information, the gender, and the age in the characteristic information of the monitored party. The computing device may introduce a probability of danger of the current location information, a probability of danger of the current time information, a probability of danger of the movement status information, a probability of danger of the gender, and a probability of danger of the age into the Bayes' theorem, and then calculate the probability of danger of the monitored party. The computing device may designate the probability of danger to the monitored party as the security status information of the monitored party.

In implementations, the computing device may access a database corresponding to the characteristic information based on a type of the characteristic information and acquire a probability of danger corresponding to the specific characteristic information of the monitored party. For example, if the age of the characteristic information of the monitored party is 23, the computing device may access a database that store danger probabilities corresponding to various ages values based on the age, and determine and acquire the probability of danger corresponding to age 23. In some implementations, the computing device may acquire corresponding data from a database of a police department, and analyze as well as organize statistical data to form a database of the characteristic information of the monitored party.

It should be noted that the computing device may introduce the acquired probabilities of danger of the various characteristic information into Bayes' theorem in the following manners. Because the equation of Bayes' theorem in the method of security prejudgment as described above (P(B|A)=P(A|B)*P(B)/P(A)) includes two variables, the computing device may change the Bayes' theorem to include more than two variables. For example, if the number of variables is three, the Bayes' theorem is represented by P(A|B,C)=P(B|A)*P(A)*P(C|A,B)/(P(B)*P(C|B)). This equation can be derived from the Bayes' theorem with two variables and definition of conditional probability. In some implementations, because the characteristic information of the monitored party has five variables, the Bayes' theorem may be changed to: P(H[i]/A)=P(H[i])*P(A|H[i])/{P(H[1]) *P(A|H[1])+P(H[2])*P(A|H[2])+P(H[n])*P(A|H[n])}, wherein n is 5.

It is understood that the computing device may introduce a probability of danger of the current location information, a probability of danger of the current time information, a probability of danger of the movement status information, a probability of danger of the gender, and a probability of danger of the age into the Bayes' theorem, and designate the probability of danger to the monitored party as the security status information of the monitored party. Therefore, the security status of the monitored party is a value between 0 and 1.

In implementations, in addition to acquiring the security status information of the monitored party using the Bayes' theorem, the computing device may acquire the security status information by comparing to predetermined comparison information, as described in more detailed below.

The computing device may acquire the security status information by comparing to predetermined comparison information in the following manners.

The computing device may acquire a predetermined prejudgment condition of the gender and age in the characteristic information of the monitored party. The predetermined prejudgment condition may include threshold time information, a speed threshold, position information of a longitudinal acceleration threshold and a preset danger area.

The computing device may map the current time information in the characteristic information of the monitored party to the threshold time information in the predetermined prejudgment condition. If the time information of the characteristic information of the monitored party is greater than the time information in the predetermined prejudgment condition, the computing device may generate an identifier for a successful match.

The computing device may map the current location information in the characteristic information of the monitored party to the predetermined danger area in the predetermined prejudgment condition. If the current location information is within the predetermined danger area in the prejudgment condition, the computing device may generate an identifier for a successful match.

The computing device may map the movement information in the characteristic information of the monitored party to the speed threshold and the longitudinal acceleration threshold in the predetermined prejudgment condition. If the movement information of the characteristic information of the monitored party is greater than the time information in the predetermined prejudgment condition, the computing device may generate an identifier for a successful match.

Based on the identifier for a successful match, the computing device may generate the security status information of the monitored party.

In implementations, the computing device may acquire a predetermined prejudgment condition of the gender and age in the characteristic information of the monitored party in the following manners. The computing device may access a database corresponding to the gender based on the gender of the monitored party. The computing device may query a database in which an age string includes the record of the age of the monitored party using the age of the monitored party. The record may include the predetermined prejudgment condition. The predetermined prejudgment condition may include threshold time information, a speed threshold, position information of a longitudinal acceleration threshold and a preset danger area.

It should be noted that the computing device may map the current location information in the characteristic information of the monitored party to the predetermined danger area in the predetermined prejudgment condition by performing the following operations. The computing device may map the current location information in the characteristic information of the monitored party to the predetermined danger area in the predetermined prejudgment condition. For example, the predetermined danger area may include a circle with a radius of 300 meters with respect to a position latitude and longitude of a dangerous area. If the current location information is within the predetermined danger area in the prejudgment condition, the computing device may map the movement information in the characteristic information of the monitored party to a speed threshold and a longitudinal acceleration threshold in the predetermined prejudgment condition by mapping the lateral acceleration information in the characteristic information of the monitored party to the acceleration thresholds in the predetermined prejudgment condition, and mapping the longitudinal acceleration information in the characteristic information of the monitored party to the longitudinal acceleration threshold in the predetermined prejudgment condition. Based on the identifier for a successful match, the computing device may generate the security status information of the monitored party. The computing device may calculate a ratio of successful matches based on a number of identifiers of the successful matches, and may generate the security status information of the monitored party. For example, the predetermined prejudgment conditions include four conditions. If the number of the identifiers of successful matches is 2, the generated security status information of the monitored party is 0.5.

Based on various ages of the monitored party in the characteristic information, if the age is younger than 12 or greater than 70, the computing device may calculate security status information of the monitored party based on a probability of danger that has been stored and corresponds to the characteristic information of the monitored party by mapping the current location information in the characteristic information of the monitored party to the resident location information of the monitored party. If the current location information is not within a predetermined range of the resident location information of the monitored party, the computing device may start a timer. If the current location information is within a predetermined range of the resident location information of the monitored party, the computing device may terminate the timer. In response to a determination that a time period recorded by the timer is greater than a predetermined time period, the computing device may generate the probability of danger to the monitored party that is greater than the first threshold, and designate the probability of danger to the monitored party as the security status information of the monitored party.

It should be noted that the resident location information of the monitored party may include the living location information, the school location information, or usually walking location information of the monitored party.

In implementations, the computing device may start a timer if the location information of the monitored party is not within a circle with a radius (e.g., 300 meters) with respect to the resident location information. Before a time period recorded by the timer is greater than a predetermined time period, the computing device may terminate the timer if the current location information becomes within the predetermined range of the resident location information of the monitored party.

For example, if the predetermined time period is an hour, the first threshold value is set to 0.7 in implementations of the method for security prejudgment based on the characteristic information. If the time period recorded by the timer is greater than an hour, the computing device may generate the probability of danger to the monitored party that is 0.8.

At S107, the computing device may perform an appropriate operation based on the determination by the following detailed operations. If the security status information is greater than a first threshold, the computing device may transmit to a predetermined monitoring party a login key used for acquiring the characteristic information of the monitored party. if the security status information is not greater than a first threshold, the computing device may transmit a prompt message generated based on characteristic information of the monitoring party to the monitored party.

It should be noted that the computing device may transmit the prompt message generated based on the characteristic information of the monitored party to the monitored party. The computing device may consider the security status information of the monitored party that is generated based on the characteristic information of the monitored party, and transmit the message corresponding to the security status information. The prompt message may include the current location information, current time information, and movement status information of the monitored party when the operation is triggered. For example, the prompt message gradually increases the intensity of the message content based on the gradient of the security status information from small to large. If the security status information of the monitored party is "0", the message content includes the prompt message indicating being safe. If the security status information is "0.6", the message content includes the prompt message that is not safe, and the prompt message may recommend going home as soon as possible.

After the monitoring party uses the login key to log on the server, the present disclosure provides a preferred implementation to more clearly acquire the trajectory of the monitored party. In some implementations, after transmitting to the predetermined monitoring party the login key used for acquiring the characteristic information of the monitored party, the computing device may record the current location information in the characteristic information of the monitored party, and designate the current location information as a trigger location information.

For example, each received current location information in the characteristic information of the monitored party is projected onto a projection coordinate.

In implementations, the computing device may process each received current location information in the characteristic information of the monitored party to project to a projection coordinate system used to represent a motion trajectory of the monitored party based on the received time sequence, and to label the recorded triggering position information of the monitored party in the projection coordinate system. For example, the projected coordinate system may adopt a map application provided by a third-party or a server terminal, and the map uses latitude and longitude as coordinates to project the current location information in the characteristic information of the monitored party.

In addition, the alarm information includes the current location information, the current time information, and the movement status information of the monitored party when the alarm is triggered when the alarm information that is sent by the monitored party.

Other operations in S107 are similar to implementations of the method for security prejudgment based on characteristic information, which is discussed in details above, and similarities are not mentioned here.

If the monitored party includes a smart device capable of monitoring health information, the method of security prejudgment based on characteristic information may be implemented using the following manners.

It should be noted that the smart device capable of monitoring health information, the computing device may include a health detection wearable device, a blood pressure meter or other medical devices for medical uses.

At S101, the computing device may receive characteristic information of a monitored party from the monitored party through GPRS\3G\4G or WIFI connection that may be established with the monitored party, and receive information of the monitored party such as a gender, an age, a heart rate, a body temperature and a respiratory rate of the monitored party.

It should be noted that the gender and age refer to the gender and age input by a user associated with the monitored party when the user uses the health detection wearable device, the blood pressure meter or the other medical devices for medical uses at the first time. The heart rate, body temperature and respiratory rate of the monitored party may be obtained by configuring sensors of the wearable device to measure bodies' characteristic parameters. For example, the wearable device may measure and/or calculate the heart rate, the body temperature, and the respiratory rate of the user.

Based on various ages of the monitored party in the characteristic information, if the age of the characteristic information of the monitored party is 75, with respect to the receiving the characteristic information of a monitored party from the monitored party at S101, the characteristic information of the monitored party may further include longitudinal acceleration.

At S103, the computer may calculate security status information of the monitored party based on a probability of danger that has been stored and corresponds to the characteristic information of the monitored party by calculating the security status information of the monitored party based on Bayes' theorem using a probability of danger that has been stored and corresponds to the characteristic information of the monitored party. Detailed operations are provided as follow.

The computing device may acquire predetermined probabilities of danger corresponding to the gender, the age, the heart rate, the body temperature and the respiration rate in the characteristic information of the monitored party, introduce a probability of danger of the gender, a probability of danger of the age, a probability of danger of the heart rate, a probability of danger of the body temperature, and a probability of danger of the respiration rate into the Bayes' theorem, calculate the probability of danger to the monitored party, and designate the probability of danger to the monitored party as the security status information of the monitored party.

In implementations, the computing device may access a database corresponding to the characteristic information based on a type of the characteristic information and acquire a probability of danger corresponding to the specific characteristic information of the monitored party. For example, if the age of the characteristic information of the monitored party is 23, the computing device may access a database that store probabilities of danger corresponding to various ages values based on the age, and determine and acquire the probability of danger corresponding to age 23. In some implementations, the computing device may acquire corresponding data from a database of a hospital database system, and analyze as well as organize statistical data to form a database of the characteristic information of the monitored party.

It should be noted that the computing device may introduce the acquired probabilities of danger of the various characteristic information into Bayes' theorem in the following manners. Because the equation of Bayes' theorem in the method of security prejudgment as described above $(P(B|A)=P(A|B)*P(B)/P(A))$ includes two variables, the computing device may change the Bayes' theorem to include more than two variables. For example, if the number of variables is three, the Bayes' theorem is represented by $P(A|B,C)=P(B|A)*P(A)*P(C|A,B)/(P(B)*P(C|B))$. This equation can be derived from the Bayes' Theorem with two variables and definition of conditional probability. In some implementations, because the characteristic information of the monitored party has five variables, the Bayes' theorem may be changed to: $P(H[i]/A)=P(H[i])*P(A|H[i])/\{P(H[1])*P(A|H[1])+P(H[2])*P(A|H[2])+\ldots+P(H[n])*P(A|H[n])\}$, wherein. n is 5.

It is understood that, the computing device may introduce a probability of danger of the gender, a probability of danger of the age, a probability of danger of the heart rate, a probability of danger of the body temperature, and a probability of danger of the respiration rate into the Bayes' theorem, and designate the probability of danger to the monitored party as the security status information of the monitored party. Therefore, the security status of the monitored party is a value between 0 and 1.

Based on various ages of the monitored party in the characteristic information, if the age of the characteristic information of the monitored party is 75, corresponding to operation S101 of receiving the longitudinal acceleration of the monitored party, the computing device may calculate the security status information of the monitored party based on the probability of danger that has been stored and corresponds to the characteristic information of the monitored party in the following manners.

The computing device may acquire a probability of danger corresponding to the longitudinal acceleration in the characteristic information of the monitored party, introduce the predetermined probability of danger corresponding to the longitudinal acceleration into Bayes' theorem, and calculate the probability of danger of the monitored party.

If the characteristic information of the monitored party includes the longitudinal acceleration, when introduced into Bayes' theorem, the characteristic information of the monitored party has five variables, and the Bayes' theorem may be changed to: $P(H[i]/A)=P(H[i])*P(A|H[i])/\{P(H[i])*P(A|H[1])+P(H[2])*P(A|H[2])+\ldots+P(H[n])*P(A|H[n])\}$, wherein n is 6.

In implementations, in addition to acquiring the security status information of the monitored party using the Bayes' theorem, the computing device may acquire the security status information by comparing to predetermined comparison information, as described in more detailed below.

The computing device may acquire the security status information by comparing to predetermined comparison information in the following manners.

The computing device may acquire a predetermined prejudgment condition of the gender and age in the characteristic information of the monitored party. The predetermined prejudgment condition may include a heart rate range, a body temperature range, a respiratory rate range.

The computing device may map the heart rate in the characteristic information of the monitored party to the heart rate range in the predetermined prejudgment condition. If the heart rate of the characteristic information of the monitored party is not within the heart rate range in the predetermined prejudgment condition, the computing device may generate an identifier for a successful match.

The computing device may map the temperature in the characteristic information of the monitored party to the temperature range in the predetermined prejudgment condition. If the temperature of the characteristic information of the monitored party is not within the temperature range in the predetermined prejudgment condition, the computing device may generate an identifier for a successful match.

The computing device may map the respiratory rate in the characteristic information of the monitored party to the respiratory rate range in the predetermined prejudgment condition. If the respiratory rate of the characteristic information of the monitored party is not within the respiratory rate range in the predetermined prejudgment condition, the computing device may generate an identifier for a successful match.

Based on the identifier for a successful match, the computing device may generate the security status information of the monitored party.

In implementations, the computing device may acquire a predetermined prejudgment condition of the gender and age in the characteristic information of the monitored party in the following manners. The computing device may, based on the gender of the monitored party, access a database corresponding to the gender. The computing device may query a database in which an age string includes the record of the age of the monitored party using the age of the monitored party. The record may include the predetermined prejudgment condition. The predetermined prejudgment condition may include a heart rate range, a body temperature range, and a respiratory rate range. For example, a male age is 65, the heart rate range is of 50 to 90, the body temperature is of 36-36.5°, and a respiratory rate is of 12-20.

It should be noted that the computing device may generate the security status information of the monitored party based on the identifier for a successful match in the following manners. The computing device may calculate a ratio of successful matches based on a number of identifiers of the successful matches, and may generate the security status information of the monitored party. For example, the predetermined prejudgment conditions include three conditions. If the number of the identifiers of successful matches is 2, the generated security status information of the monitored party is 0.66.

Based on various ages of the monitored party in the characteristic information, if the age of the characteristic information of the monitored party is 75, corresponding to operation S101 of receiving the longitudinal acceleration of the monitored party, the computing device may calculate the security status information of the monitored party based on the probability of danger that has been stored and corresponds to the characteristic information of the monitored party in the following manners.

When the computing device acquires a predetermined prejudgment condition of the gender and age in the characteristic information of the monitored party, the predetermined prejudgment condition may include a longitudinal acceleration threshold.

The computing device may map the longitudinal acceleration information in the characteristic information of the monitored party to the longitudinal acceleration threshold in the predetermined prejudgment condition. If the longitudinal acceleration of the characteristic information of the monitored party is greater than the longitudinal acceleration threshold in the predetermined prejudgment condition, the computing device may generate an identifier for a successful match.

At S107, the computing device may perform an appropriate operation based on the determination by the following detailed operations. If the security status information is greater than a first threshold, the computing device may transmit to a predetermined monitoring party a login key used for acquiring the characteristic information of the monitored party; if the security status information is not greater than a first threshold, the computing device may transmit a prompt message generated based on characteristic information of the monitoring party to the monitored party.

It should be noted that the computing device may transmit the prompt message generated based on the characteristic information of the monitored party to the monitored party, the computing device may consider the security status information of the monitored party that is generated based on the characteristic information of the monitored party, and transmit the message corresponding to the security status information. The prompt message may include the heart rate, the body temperature and the respiratory rate of the monitored party when the operation is triggered. For example, the prompt message gradually increases the intensity of the message content based on the gradient of the security status information from small to large. If the security status information of the monitored party is "0", the message content includes the prompt message indicating being healthy. If the security status information is "0.6", the message content includes the prompt message indicating that the heart rate or respiratory rate is too fast or the body temperature is too high or low.

After transmitting to the predetermined monitoring party a login key used for acquiring the characteristic information of the monitored party, the visualization of the monitored party may be generated by the server terminal based on the characteristic information. When the characteristic information of the monitored party includes a heart rate, a body temperature and a respiratory rate, the visualization may include figures indicating changes of the heart rate, the body temperature and the respiratory rate in a predetermined time period. For example, the computing device may generate the figures associated with the heart rate, the body temperature and the respiratory rate in three hours.

In addition, when the alarm information that is sent by the monitored party, the alarm information includes the heart rate, the body temperature, and the respiratory rate of the monitored party when the alarm is triggered.

Other operations in S107 are similar to implementations of the method for security prejudgment based on characteristic information, which is discussed in details above, and similarities are not mentioned here.

If the monitored party includes a sensor device capable of detecting a physical parameter, the method of security prejudgment based on characteristic information may be implemented in the following manners.

It should be noted that a sensor device capable of detecting a physical parameter may include a temperature sensor, a light sensor, a volume sensor, a gas sensor or other applications in smart home sensors, for example, a security door sensor.

At S101, the computing device may receive characteristic information of a monitored party from the monitored party via GPRS\3G\4G or WIFI connections that may be established with the monitored party, and the computing device may receive information of the monitored party such as a temperature, brightness, or a gas concentration.

At S103, the computer may calculate security status information of the monitored party based on a probability of danger that has been stored and corresponds to the characteristic information of the monitored party by calculating the security status information of the monitored party based on Bayes' theorem using a probability of danger that has been stored and corresponds to the characteristic information of the monitored party. Detailed operations are provided as follow.

The computing device may acquire predetermined probabilities of danger corresponding to the temperature, the brightness, the volume, and/or the gas concentration in the characteristic information of the monitored party.

The computing device may introduce a probability of danger of the temperature, a probability of danger of the brightness, a probability of danger of the volume, and a probability of danger of the gas concentration into the Bayes' theorem, calculate the probability of danger to the monitored party, and designate the probability of danger to the monitored party as the security status information of the monitored party.

In implementations, the computing device may access a database corresponding to the characteristic information based on a type of the characteristic information and acquire a probability of danger corresponding to the specific characteristic information of the monitored party. For example, if the temperature of the characteristic information of the monitored party is 25°, the computing device may access a database that store probabilities of danger corresponding to various temperature values based on the temperature. The computing device may determine and acquire the probability of danger corresponding to 25°. In some implementations, the computing device may acquire corresponding data from a database of a fire protection system, and analyze as well as organize statistical data to form a database of the characteristic information of the monitored party.

It should be noted that the computing device may introduce the acquired probabilities of danger of the various characteristic information into Bayes' theorem in the following manners. Because the equation of Bayes' theorem in the method of security prejudgment as described above (P(B|A)=P(A|B)*P(B)/P(A)) includes two variables, the computing device may change the Bayes' theorem to include more than two variables. For example, if the number of variables is three, the Bayes' theorem is represented by P(A|B,C)=P(B|A)*P(A)*P(C|A,B)/(P(B)*P(C|B). This equation can be derived from the Bayes' Theorem with two variables and definition of conditional probability. In some implementations, because the characteristic information of the monitored party has four variables, the Bayes' theorem may be changed to: P(H[i]/A)=P(H[i])*P(A|H[i])/{P(H[1]) *P(A|H[1])+P(H[2])*P(A|H[2])+ . . . +P(H[n])*P(A|H[n])}, wherein n is 4.

It is understood that, the computing device may introduce a probability of danger of the temperature, a probability of danger of the brightness, a probability of danger of the volume, and a probability of danger of the gas concentration into the Bayes' theorem, and designate the probability of danger to the monitored party as the security status information of the monitored party. Therefore, the security status of the monitored party is a value between 0 and 1.

In implementations, in addition to acquiring the security status information of the monitored party using the Bayes' theorem, the computing device may acquire the security status information by comparing to predetermined comparison information, as described in more detailed below.

The computing device may acquire the security status information by comparing to predetermined comparison information in the following manners.

The computing device may acquire a predetermined prejudgment condition of the characteristic information of the monitored party. The predetermined prejudgment condition may include a temperature range, a luminance range, a volume and a threshold of a gas concentration.

The computing device may map the temperature information in the characteristic information of the monitored party to the temperature range in the predetermined prejudgment condition. If the temperature of the characteristic information of the monitored party is not within the temperature range in the predetermined prejudgment condition, the computing device may generate an identifier for a successful match.

The computing device may map the brightness in the characteristic information of the monitored party to the brightness range in the predetermined prejudgment condition. If the brightness of the characteristic information of the monitored party is not within the brightness range in the predetermined prejudgment condition, the computing device may generate an identifier for a successful match.

The computing device may map the volume in the characteristic information of the monitored party to the volume range in the predetermined prejudgment condition. If the volume of the characteristic information of the monitored party is not within the volume range in the predetermined prejudgment condition, the computing device may generate an identifier for a successful match.

The computing device may map the gas concentration in the characteristic information of the monitored party to the gas concentration range in the predetermined prejudgment condition. If the gas concentration of the characteristic information of the monitored party is not within the gas concentration range in the predetermined prejudgment condition, the computing device may generate an identifier for a successful match.

Based on the identifier for a successful match, the computing device may generate the security status information of the monitored party.

In implementations, the computing device may acquire a predetermined prejudgment condition of the characteristic information of the monitored party in the following manners. The computing device may access a database that store probabilities of danger corresponding to various temperature values based on the temperature, and acquire a probability of danger corresponding to the temperature in the characteristic information of the monitored party. Further, the computing device may access a database that store probabilities of danger corresponding to various brightness values based on the brightness, and acquire a probability of danger corresponding to the brightness in the characteristic information of the monitored party. The computing device may access a database that store probabilities of danger corresponding to various volume values based on the volume, and acquire a probability of danger corresponding to the volume in the characteristic information of the monitored party. The computing device may access a database that store probabilities of danger corresponding to various gas concentration values based on the gas concentration. The computing device may query a database in which a gas concentration range of gas concentration strings include the record of the gas concentration of the monitored party using the gas concentration of the monitored party, and acquire a probability of danger corresponding to the specific characteristic information of the monitored party. For example, the range of volume of the prejudgment conditions is 10-80 db, a Cot concentration threshold of 1600 ppm, a brightness range is 100-150LX, and a temperature range is 20-28°.

It should be noted that the computing device may generate the security status information of the monitored party based on the identifier for a successful match. For example, the computing device may calculate a ratio of successful matches based on a number of identifiers of the successful matches, and may generate the security status information of the monitored party. For example, the predetermined prejudgment conditions include four conditions. If the number of the identifiers of successful matches is 3, the generated security status information of the monitored party is 0.75.

At S107, the computing device may perform an appropriate operation based on the determination in the following manners.

If the security status information is greater than a first threshold, the computing device may transmit to a predetermined monitoring party a login key used for acquiring the characteristic information of the monitored party; if the security status information is not greater than a first threshold, the computing device may transmit a prompt message generated based on characteristic information of the monitoring party to the monitored party.

It should be noted that the computing device transmits the prompt message generated based on the characteristic information of the monitored party to the monitored party. The computing device may consider the security status information of the monitored party that is generated based on the characteristic information of the monitored party, and transmit the message corresponding to the security status information. The prompt message may include the temperature, the brightness, or the gas concentration of the monitored party when the operation is triggered. For example, the prompt message gradually increases the intensity of the message content based on the gradient of the security status information from small to large. If the security status information of the monitored party is "0", the message content includes the prompt message indicate that the indoor environment is safe. If the security status information is "0.6", the message content includes the prompt message indicating that the temperature is too high or low, the brightness is too high or low, the gas concentration is too high or low, or the volume is too high or low.

After transmitting to the predetermined monitoring party a login key used for acquiring the characteristic information of the monitored party, the visualization of the monitored party may be generated by the server terminal based on the characteristic information. When the characteristic information of the monitored party includes a temperature, brightness, a volume, or a gas concentration, the visualization may include figures indicating changes of the temperature, the brightness, the volume, or the gas concentration in a predetermined time period. For example, the computing device may generate the figures associated with the temperature, the brightness, the volume, or the gas concentration in three hours.

In addition, when the alarm information that is sent by the monitored party, the alarm information includes the temperature, the brightness, the volume, or the gas concentration of the monitored party when the alarm is triggered.

Other operations in S107 are similar to implementations of the method for security prejudgment based on characteristic information, which is discussed in details above, and similarities are not mentioned here.

Implementations of the present disclosure relate to a method of security prejudgment based on the characteristic information. The computing device may receive characteristic information of a monitored party from the monitored party, calculate security status information of the monitored party based on a probability of danger that has been stored and corresponds to the characteristic information of the monitored party, determine that the security status information is greater than a first threshold, and perform an appropriate operation based on the determination. The technical solution of the present disclosure solves a problem that preset monitoring conditions cannot cover potential surrounding risks that result in a safety hazard. Further, the technical solution can monitor risks that are not reflected by spatial information. By identifying and pre-warning the characteristic information, potential risks may be avoided before occurring, improving personal safety and protecting property.

The above-described implementations relate to a method of security prejudgment based on the characteristic information. Corresponding to the method of security prejudgment based on the characteristic information as described above, some implementations of the present disclosure relate to a device of security prejudgment based on the characteristic information. Since the device is substantially similar to the method described above, it is the relatively simple description. By referring parts of the method implementations, the following description of the implementations is merely illustrative.

Figure 4:
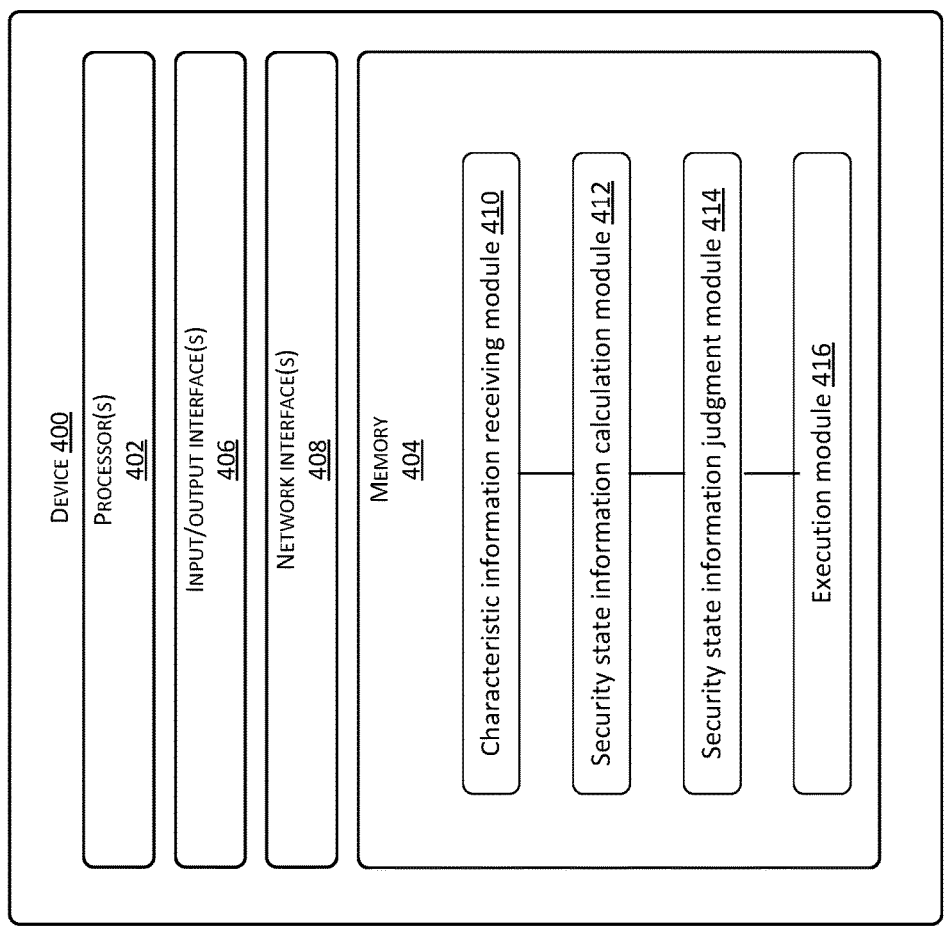
FIG. 4 is a schematic diagram illustrating a device for security prejudgment based on characteristic information in accordance with the implementations of the present disclosure.

FIG. 4 is a schematic diagram illustrating a device 400 for security prejudgment based on characteristic information in accordance with the implementations of the present disclosure.

The device 400 may include one or more processor(s) 402 or data processing unit(s) and memory 404. The device 400 may further include one or more input/output interface(s) 406, and network interface(s) 408. The memory 404 is an example of computer readable media.

The memory 404 may store therein a plurality of modules or units including a characteristic information receiving module 410, a security state information calculation module 412, a security state information judgment module 414, and an execution module 416.

The characteristic information receiving module 410 may be configured to receive characteristic information of a monitored party from the monitored party.

The security state information calculation module 412 may be configured to calculate security status information of the monitored party based on a probability of danger that has been stored and corresponds to the characteristic information of the monitored party.

The security state information judgment module 414 may be configured to determine whether the security status information is greater than a first threshold The execution module 416 may be configured to perform an appropriate operation based on the determination.

In implementations, the security state information calculation module 412 may be configured to calculate the security status information of the monitored party based on Bayes' theorem using a probability of danger that has been stored and corresponds to the characteristic information of the monitored party.

In implementations, the execution module 416 may include a login key sending sub-module configured to receive a determining result from a first threshold judgment sub-module. If the security status information is greater than a first threshold, the computing device may transmit to a predetermined monitoring party a login key used for acquiring the characteristic information of the monitored party. The execution module 416 may further include a prompt message sending sub-module configured to configured to receive a determining result from a first threshold judgment sub-module. If the security status information is not greater than a first threshold, the computing device may transmit a prompt message generated based on characteristic information of the monitoring party to the monitored party.

In implementations, the login key sending sub-module may be configured to transmit to the predetermined monitoring party the login key used for acquiring the characteristic information of the monitored party via an SMS text message.

In implementations, the execution module 416 may further include a real-time command sending sub-module configured to transmit to the predetermined monitoring party the login key used for acquiring the characteristic information of the monitored party, and then transmit an instruction to the monitored party to set a predetermined time interval for acquiring characteristic information as real-time access.

In implementations, the execution module 416 may further include a second threshold judgment sub-module configured to transmit the prompt message generated based on the characteristic information of the monitored party to the monitored party after determining that the security status information is greater than a second threshold, a message triggering sub-module configured to receive a determining result from the second threshold judgment sub-module and to trigger the prompt message sending sub-module if the determining result is positive, and an extension instruction sending sub-module configured to receive a determining result from the second threshold judgment sub-module and transmit an instruction to the monitored party to extend a predetermined time interval for acquiring characteristic information if the determining result is negative.

In implementations, the device may further include an alarm information receiving module configured to receive alarm information from the monitored party and a login key sending sub-module triggering module configured to trigger the login key sending sub-module.

In implementations, if the monitored party is a mobile terminal, the characteristic information receiving module 410 may be configured to receive the characteristic information of the monitored party including at least one of current location information, current time information, movement status information, a gender, or an age.

In implementations, the security state information calculation module 412 may include a danger probability acquisition sub-module configured to acquire predetermined probabilities of danger corresponding to the current location information, the current time information, the movement status information, the gender, and the age in the characteristic information of the monitored party, a probability calculation sub-module configured to introduce a probability of danger of the current location information, a probability of danger of the current time information, a probability of danger of the movement status information, a probability of danger of the gender, and a probability of danger of the age into the Bayes' theorem, and to calculate the probability of danger to the monitored party, and a security state information generation sub-module configured to designate the probability of danger to the monitored party as the security status information of the monitored party.

In implementations, the security state information calculation module 412 may include a matching sub-module configured to map the current location information in the characteristic information of the monitored party to the resident location information of the monitored party, a timer starting sub-module configured to start a timer if the current location information is not within a predetermined range of the resident location information of the monitored party, a timer termination sub-module configured to terminate the timer if the current location information is within a predetermined range of the resident location information of the monitored party, and a first probability generating sub-module configured to generate the probability of danger to the monitored party that is greater than the first threshold in response to a determination that a time period recorded by the timer is greater than a predetermined time period, and to designate the probability of danger to the monitored party as the security status information of the monitored party.

In implementations, the execution module 416 may further include a location information recording sub-module configured to transmit to the predetermined monitoring party the login key used for acquiring the characteristic information of the monitored party, record the current location information in the characteristic information of the monitored party, and designate the current location information as a trigger location information. The execution module 416 may further include a coordinate system projection sub-module configured to project each received current location information in the characteristic information of the monitored party onto a projection coordinate.

In implementations, the device may further include an alarm information receiving module configured to receive alarm information from the monitored party, which may include at least one of: current location information, current time information, movement status information, a gender, or an age.

In implementations, the characteristic information receiving module 410 may be configured to receive the characteristic information of the monitored party including at least one of a gender, an age, a heart rate, a body temperature, or a respiration rate if the monitored party includes a smart device capable of monitoring health information.

In implementations, the security state information calculation module 412 may include a danger probability acquisition sub-module configured to acquire predetermined probabilities of danger corresponding to the gender, the age, the heart rate, the body temperature and the respiration rate in the characteristic information of the monitored party, and a probability calculation sub-module configured to introduce a probability of danger of the gender, a probability of danger of the age, a probability of danger of the heart rate, a probability of danger of the body temperature, and a probability of danger of the respiration rate into the Bayes' theorem, and calculate the probability of danger of the monitored party. The security state information calculation module 412 may further include a security state information generation sub-module configured to designate the probability of danger to the monitored party as the security status information of the monitored party.

In implementations, the security state information calculation module 412 may be configured to further receive longitudinal acceleration.

The security state information calculation module may include a longitudinal acceleration risk probability acquisition sub-module configured to acquire a probability of danger corresponding to the longitudinal acceleration in the characteristic information of the monitored party.

In implementations, the device may further include an alarm information receiving module configured to receive alarm information from the monitored party, which includes at least one of: a heart rate, a body temperature, or a respiratory rate.

In implementations, the characteristic information receiving module 410 may be configured to receive the characteristic information of the monitored party including at least one of a temperature, brightness, a volume or a gas concentration if the monitored party includes a sensor device capable of detecting a physical parameter.

In implementations, the security state information calculation module 412 may include a danger probability acquisition sub-module configured to acquire predetermined probabilities of danger corresponding to the temperature, the brightness, the volume, the gas concentration in the characteristic information of the monitored party, a probability calculation sub-module configured to introduce a probability of danger of the temperature, a probability of danger of the brightness, a probability of danger of the volume, and a probability of danger of the gas concentration into the Bayes' theorem and to calculate the probability of danger to the monitored party, and a security state information generation sub-module configured to designate the probability of danger to the monitored party as the security status information of the monitored party.

In implementations, the device 400 may further include an alarm information receiving module (not shown in FIG. 4) configured to receive alarm information from the monitored party, which may include at least one of: a temperature, brightness, a volume or a gas concentration.

The above-described implementations relate to a method of security prejudgment based on characteristic information and a system for security prejudgment based on characteristic information to solve problems in the conventional techniques. In addition, the implementations further relate to an electronic device.

Figure 5:
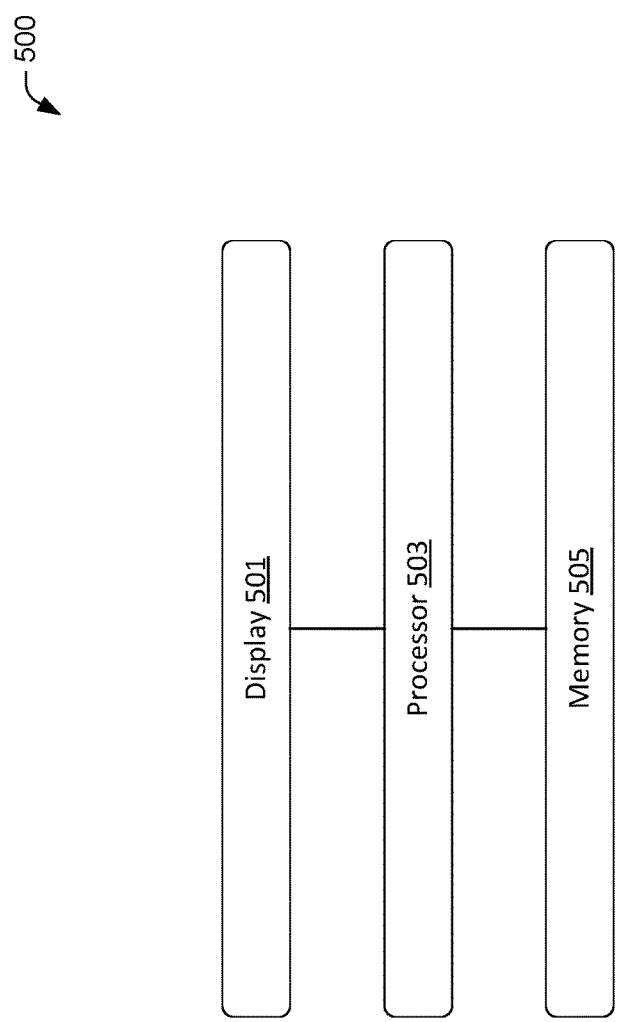
FIG. 5 is a schematic diagram illustrating an electronic device in accordance with the implementations of the present disclosure.

FIG. 5 is a schematic diagram illustrating an electronic device 500. The electronic device 500 may include a display 501, a processor 503, and memory 505 configured to store a characteristic information prejudgment program, executed by the one or more processors to: receive characteristic information of a monitored party from the monitored party, calculate security status information of the monitored party based on a probability of danger that has been stored and corresponds to the characteristic information of the monitored party, determine that the security status information is greater than a first threshold, and perform an appropriate operation based on the determination. The memory 505 is an example of computer readable media.

The above-described implementations relate to a method of security prejudgment based on characteristic information and a system for security prejudgment based on characteristic information to solve problems in the conventional techniques, and an electronic device thereof. In addition, some implementations of the present disclosure relate to a method of acquiring characteristic information.

Figure 6:
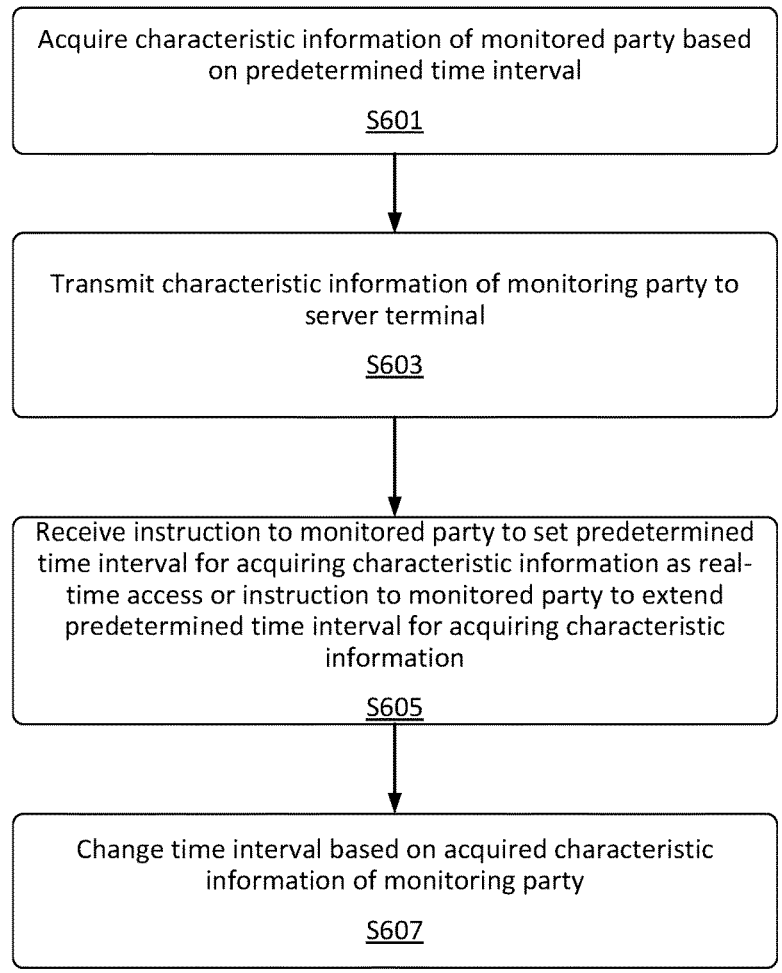
FIG. 6 is a flowchart illustrating a method of acquiring characteristic information in accordance with the implementations of the present disclosure.

FIG. 6 is a flowchart illustrating a method of acquiring characteristic information in accordance with the implementations of the present disclosure. The method may include the following operations.

At S601, the computing device may acquire the characteristic information of a monitored party based on a predetermined time interval. If the monitored party is a mobile terminal, the computing device may acquire the characteristic information of a monitored party based on a predetermined time interval by acquiring current location information, current time information, and movement status information of the monitored party based on the predetermined time interval. For example, the monitored party is a mobile phone.

The current location information may be acquired in the following manners. The current location information may be acquired using a GPS, based on base stations, or based on AGPS positioning.

When acquiring the location information of the monitored party using the GPS, the computing device may determine whether the GPS module is turned on or off. If the GPS module is turned on, a positioning mode is entered, the positioning function is turned on, and current latitude and longitude location information of the monitored party is generated. If the GPS module is turned off, the base station positioning function of the monitored party is then used.

When acquiring the location information of the monitored party using the base stations, the monitored party may search signals from all the base stations and connect to a base station with the strongest signals to acquire information of the base station and to transmit information of other base stations to a server providing services related to base station positioning. The server has latitude and longitude information of these base stations, use a triangulation positioning method to generate the latitude and longitude information of the monitored party, and use a triangulation positioning method to generate the latitude and longitude information of the monitored party. These operations may be implemented by performing the triangulation positioning using three base stations close to the monitored party. Since the position of each base station is fixed, the latitude and longitude coordinates of the monitored party may be calculated using transmission times of electromagnetic waves among these three base stations.

When acquiring the location information of the monitored party using the AGPS, information of the connected base stations may be transmitted to a server providing services related to base station positioning through the network. GPS assistance information of the location of the monitored party may be received from the server, the monitored party may receive original GPS signals based on the GPS assistance information, the monitored party then may demodulate the original GPS signals after receiving the original GPS signals, calculate satellite pseudoranges from the monitored party, and transmit the location information to the server via the network. The server may estimate the location of the monitored party based on the satellite pseudoranges from the monitored party and the GPS assistance information.

It should be noted that, if the monitored party includes GPS hardware, positioning may be performed without the network. The base station positioning may be performed using multiple base stations and the distances between the monitored party and the base stations to determine the location of the monitored party, and then the server may transmit the location information to the monitored party. AGPS assists the GPS function, and may be used without GPS modules via a data network or wireless WIFI to achieve the position function. When the monitored party is out of the coverage of the network, the AGPS function may not be implemented. AGPS is new technology that combines satellite positioning technology and mobile wireless cellular technology. In other words, AGPS implements positioning by combining the GPS and the monitored party. As compared to GPS positioning technology, AGPS reduces the time required to determine the location. When the monitored party includes a GPS module and is out of the coverage of the network, the order of latitude and longitude location information that is generated by a GPS and base stations is provided as follow. The GPS positioning is dominated for outdoors since signals of the GPS is stronger. For indoors or an area with weak signals, the base station positioning is dominated.

It should be noted that the location information of the monitoring party includes latitude and longitude information of the monitored party or a coding string of geophash of a location (a type of address coding). In some implementations, the location information may be determined using landmarks such as concrete buildings.

The current time information of the monitored party may be acquired in the following manners. The computing device may acquire the current time of the monitored party using an interface provided by the system. For example, the computing device may use applications (e.g., Calendar) to acquire the current time of the monitored party.

The movement status information of the monitored party may be acquired in the following manners. The computing device may acquire the movement status information using a three-axis acceleration sensor to collect acceleration and directions of motion of the monitored party.

When collecting the acceleration of the monitored party using the three-axis acceleration sensor, signals of gravity acceleration may be detected by the three-axis acceleration sensor, lateral acceleration of the monitored party may be calculated by based on the X-axis acceleration and Y-axis acceleration, and longitudinal acceleration of the monitored party may be calculated based on the Z-axis acceleration.

In implementations, the X-axis acceleration, Y-axis acceleration, and Z-axis acceleration that are collected by the three-axis acceleration sensor may be converted to physical coordinates. The computing device may calibrate the X-axis acceleration, Y-axis acceleration, and Z-axis acceleration to obtain monitoring data of the movement status information of the monitored party.

Based on the relationship between the acquired location information of the monitored party and the current time, the computing device may calculate the velocity of the monitored party. For example, the computing device may acquire the movement distance based on the acquired location information the monitored party, and may calculate the velocity of the monitored party based on the time information when the monitored party is at the starting point and the end point.

To improve the accuracy of the collected information of the monitored party, the present disclosure provides a preferred implementation before acquiring the characteristic information of the monitored party based on the predetermined time interval. In some implementations, the computing device may receive input of a gender, an age, and resident location information on the monitoring party.

In implementations, the computing device may receive input of a gender, an age, and resident location information on the monitoring party in the following manners. The computing device may display a text input window, and display a virtual keyboard on the display, and receive user touch operations on the virtual keyboard associated with information such as a gender, an age, and resident location information on the monitoring party. For example, the resident location information may include latitude and longitude information or a coding string of geophash of a location (a type of address coding). In some implementations, the location information may be determined using landmarks such as concrete buildings.

If the monitored party includes a smart device capable of monitoring health information, the computing device may acquire the characteristic information of a monitored party based on a predetermined time interval by acquiring a heart rate, a body temperature, a respiratory rate and longitudinal acceleration of the monitoring party based on a predetermined time interval.

It should be noted that the smart device capable of monitoring health information may include a health detection wearable device, a blood pressure meter or other medical devices for medical uses.

The characteristic information of the monitored party may be obtained by configuring sensors of the wearable device to measure bodies' characteristic information and by estimating or collecting the characteristic parameters. The characteristic information may include at least one of a heart rate, a body temperature, a respiratory rate and longitudinal acceleration of the monitoring party. For example, the wearable device may measure and/or calculate the heart rate, the body temperature, the respiratory rate of the user, longitudinal acceleration et al. To obtain the characteristic information, corresponding sensors in the wearable device may be configured, for example a pulse sensor, a temperature sensor, a gravity sensor et al. Those skilled in the art may configure the sensors based on the characteristic information. In addition to the method above, other body's characteristic information may further be used based on various detecting devices of the monitored party. For example, a video recording device may be used to acquire information such as states of open and closed eyes, movement of the eyeball and other characteristic information that reflects the state of consciousness of a person.

Before acquiring the characteristic information of the monitored party based on the predetermined time interval, the monitored party may include a smart device capable of monitoring health information, and receive input of a gender and an age on the monitoring party in the following manners. The computing device may display a text input window, and display a virtual keyboard on the display, and receive user touch operations on the virtual keyboard to input the gender and the age.

If the monitored party includes a sensor device capable of detecting a physical parameter, the computing device may acquire the characteristic information of a monitored party based on a predetermined time interval. For example, the computing device may acquire a temperature, brightness, a volume, or a gas concentration of the monitored party based on a predetermined time interval.

The temperature of the monitored party may be acquired using a temperature sensor. By having two different conductor or semiconductor materials welded together, a closed circuit is constituted. When temperature differences between two attachment points of the conductor, electromotive force arises between the two attachment points and thus forms a current in the circuit. This phenomenon is called pyroelectric effect. Thermocouple temperature sensor is designed to implement this effect. Commonly thermocouple temperature sensor can be measured from minus 50 degrees to 1600 degrees, while some may reach negative 269 degrees or 2800 degrees.

The brightness of the monitored party may be measured using visible light sensors or optical acquisition sensors. Photodiodes may detect light intensity including visible light and infrared illumination and light intensity of the infrared illumination. The light intensity is then converted to 16-bit, I2C standard digital signals for output.

The volume of the monitored party may be obtained a voice sensor, including an audio amplifier, a frequency-selective circuit, an time-delay control circuit and a thyristor gating circuit.

The gas concentration of the monitored party may be obtained using a gas sensor, which converts a fraction of the volume of a gas into a corresponding electrical signal to represent the gas concentration. The probe may process gas samples using a gas sensor gas, for example, filtering out impurities and interfering gases, drying or cooling processes, and displaying.

At S603, the computing device may transmit the characteristic information of the monitoring party to a server terminal.

In implementations, after acquiring the characteristic information of the monitored party based on the predetermined time interval, operation S603 may be performed to transmit the acquired characteristic information of the monitored party to the server terminal. The computing device may transmit the characteristic information of the monitoring party to the server terminal via GPRS\3G\4G or WIFI connections that may be established with the monitored party to transmit the characteristic information of the monitoring party to a server terminal.

It is understood that the transmitted characteristic information may vary based on the type of the monitored party. If the monitored party is a mobile terminal, the computing device may transmit current location information, current time information, movement status information, an age, and a gender of the monitored party; if the monitored party includes a smart device capable of monitoring health information, the computing device may transmit a heart rate, a body temperature, a respiratory rate of the monitored party to the server terminal; if the monitored party includes a sensor device capable of detecting a physical parameter, the computing device may transmit a temperature, brightness, or a gas concentration of the monitored party.

To reduce the amount of data transferred between the monitored party and the server terminal, the present disclosure provides a preferred implementation. In some implementations, when the monitored party includes a mobile device or a smart device capable of monitoring health information, only when the monitored party and the server terminal establish a connection at the first time, the monitored party may transmit the age and the gender in the characteristic information of the monitored party.

It is understood that, because the age and the gender in the characteristic information of the monitored party don't change in a very long time period (e.g., a year), when transmitting data between the monitored party and the server terminal, a large amount of duplicated information may be transmitted to the server terminal. Therefore, when the monitored party and the server terminal establish a connection at the first time, the monitored party may transmit the age and the gender in the characteristic information of the monitored party.

To update the age in the characteristic information of the monitored party, the updated age may be calculated based on the current time of the monitored party. When the monitored party detects the update of the monitored party, at the next communication with the server terminal, the updated age may be transmitted to the monitored party.

In implementations, in addition to transmitting the characteristic information of the monitoring party to a server terminal after acquiring the characteristic information of a monitored party based on a predetermined time interval, an active triggering alarm operation may be performed to transmit the characteristic information of the monitored party to the server terminal, as described in S701 to S705.

Figure 7:
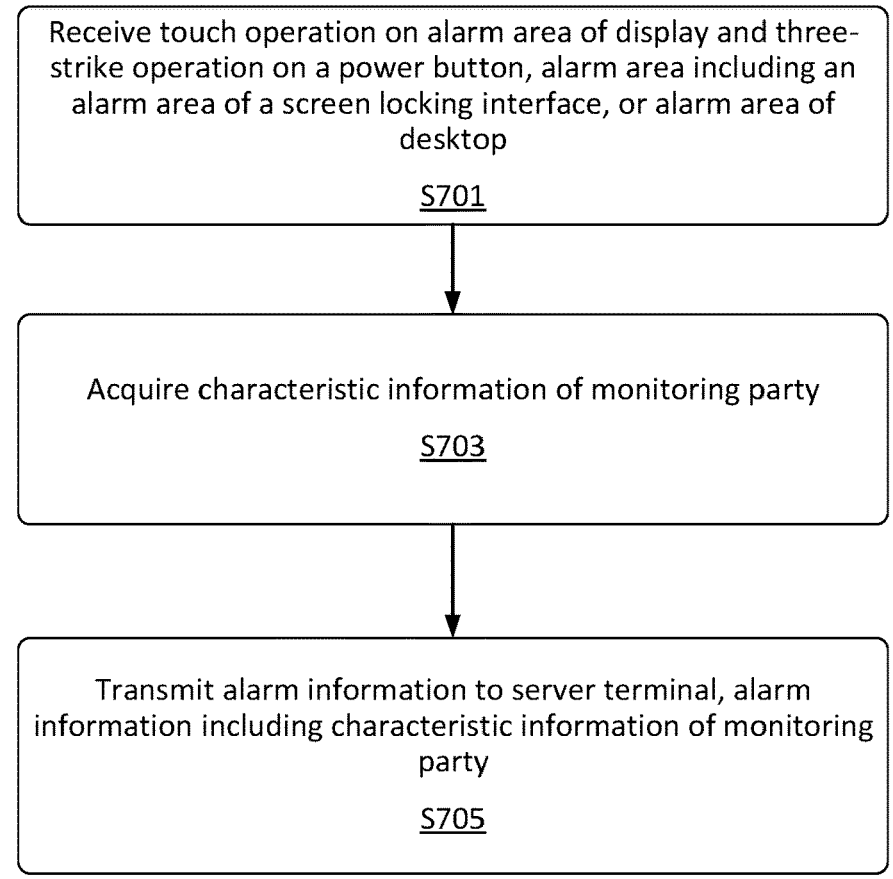
FIG. 7 is a flowchart illustrating a process of an active triggering alarm operation to transmit characteristic information of a monitored party to a server terminal in accordance with the implementations of the present disclosure.

FIG. 7 is a flowchart illustrating a process of an active triggering alarm operation to transmit characteristic information of a monitored party to a server terminal in accordance with the implementations of the present disclosure.

At S701, the computing device may receive a touch operation on an alarm area of the display and a three-strike operation on a power button. The alarm area may include an alarm area of a screen locking interface, or an alarm area of a desktop.

In implementations, when the monitored party includes a mobile device or a smart device capable of monitoring health information, the alarm of the desktop is a replacement of a desktop icon or a button of the original emergency call of the monitored party on the lock screen.

At S703, the computing device may acquire the characteristic information of the monitoring party.

In these instances, this operation is similar to those described in operation S601 with respect to acquiring the characteristic information of the monitored party.

It should be noted that, if the monitored party is a mobile terminal, the characteristic information of the monitored party may include: current location information, current time information, movement status information, gender, and age; if the monitored party includes a smart device capable of monitoring health information, the characteristic information of the monitored party may include: a heart rate, a body temperature, a respiratory rate and longitudinal acceleration; if the monitored party includes a sensor device capable of detecting a physical parameter, the characteristic information of the monitored party may include: a temperature, brightness, a volume or a gas concentration.

At S705, the computing device may transmit the alarm information to the server terminal. The alarm information may include the characteristic information of the monitoring party.

In implementations, the alarm information may include the characteristic information of the monitoring party, which is acquired at S703.

To increase a rescue probability in response to triggering the alarm information, the present disclosure provides a preferred implementation. In some implementations, with respect to the transmitting the alarm information to the server terminal, the computing device may transmit contact information to the monitored party and the alarm information to a map application.

It should be noted that the computing device may transmit the alarm information to the contact of the monitored party in the following manners. The computing device may enable transmitting the alarm information to contacts in the contact of the monitored party and/or contacts of the contact of a mobile messaging application.

In addition, after transmitting the characteristic information of the monitoring party to the server terminal, the computing device may receive a prompt message generated based on characteristic information of the monitoring party to from the server terminal.

It should be noted that the computing device may consider the security status information of the monitored party that is generated based on the characteristic information of the monitored party, and transmit the message corresponding to the security status information. For example, the prompt message gradually increases the intensity of the message content based on the gradient of the security status information from small to large. If the security status information of the monitored party is "0", the message content includes the prompt message indicating being safe. If the security status information is "0.6", the message content includes the prompt message that is not safe, and the prompt message may recommend going home as soon as possible.

At S605, the computing device may receive an instruction to the monitored party to set a predetermined time interval for acquiring characteristic information as real-time access or an instruction to the monitored party to extend a predetermined time interval for acquiring characteristic information.

In implementations, a computing device may receive an instruction to the monitored party to set a predetermined time interval for acquiring characteristic information as real-time access or an instruction to the monitored party to extend a predetermined time interval for acquiring characteristic information via a connection such as GPRS \\ 3G\\ 4G or WIFI between the monitored party and the server terminal.

It should be noted that the instruction to the monitored party to set a predetermined time interval for acquiring characteristic information may include: setting the time interval for acquiring characteristic information to 1 second. The instruction to the monitored party to extend a predetermined time interval for acquiring characteristic information may include: extending the predetermined time interval for acquiring the characteristic information based on the security status information.

At S607, the computing device may change the time interval based on the acquired characteristic information of the monitoring party.

In implementations, a computing device may receive an instruction to the monitored party to set a predetermined time interval for acquiring characteristic information as real-time access or an instruction to the monitored party to extend a predetermined time interval for acquiring characteristic information at S605 and to set the time interval for acquiring characteristic information using the time interval in the instruction.

For example, if the time interval for acquiring characteristic information for the monitored party is 60 seconds, and the predetermined time period for acquiring the characteristic information in the instruction is 5 minutes, the computing device may set the time interval for acquiring characteristic information from 60 seconds to 300 seconds. If the computing device receives the instruction to set a predetermined time interval for acquiring characteristic information as real-time access, the computing device may set the time interval for acquiring characteristic information from 60 seconds to 1 second.

In implementations, the computing device may acquire the characteristic information of a monitored party based on a predetermined time interval using a timer such that when a time period recorded by the timer is equal to a predetermined time period, the computing device may acquire the characteristic information. In these instances, the computing device may change the time interval based on the acquired characteristic information of the monitoring party by changing the time of the timer.

Implementations of the present disclosure relate to a method of acquiring characteristic information. The method may include acquiring the characteristic information of a monitored party based on a predetermined time interval, transmitting the characteristic information of the monitoring party to a server terminal, and receiving an instruction to the monitored party to set a predetermined time interval for acquiring characteristic information as real-time access or an instruction to the monitored party to extend a predetermined time interval for acquiring characteristic information. The computing device may change the time interval based on the acquired characteristic information of the monitoring party. The technical solution solves the problem of data traffic waste caused by wireless data communication and transmission when monitoring a target for a long time.

The above-described implementations provide a method for acquiring characteristic information. Corresponding to the method above, some implementations of the present disclosure relate to a device for acquiring characteristic information. Since the implementations of the device are substantially similar to those of the method described above, the following descriptions of the implementations are merely illustrative.

Figure 8:
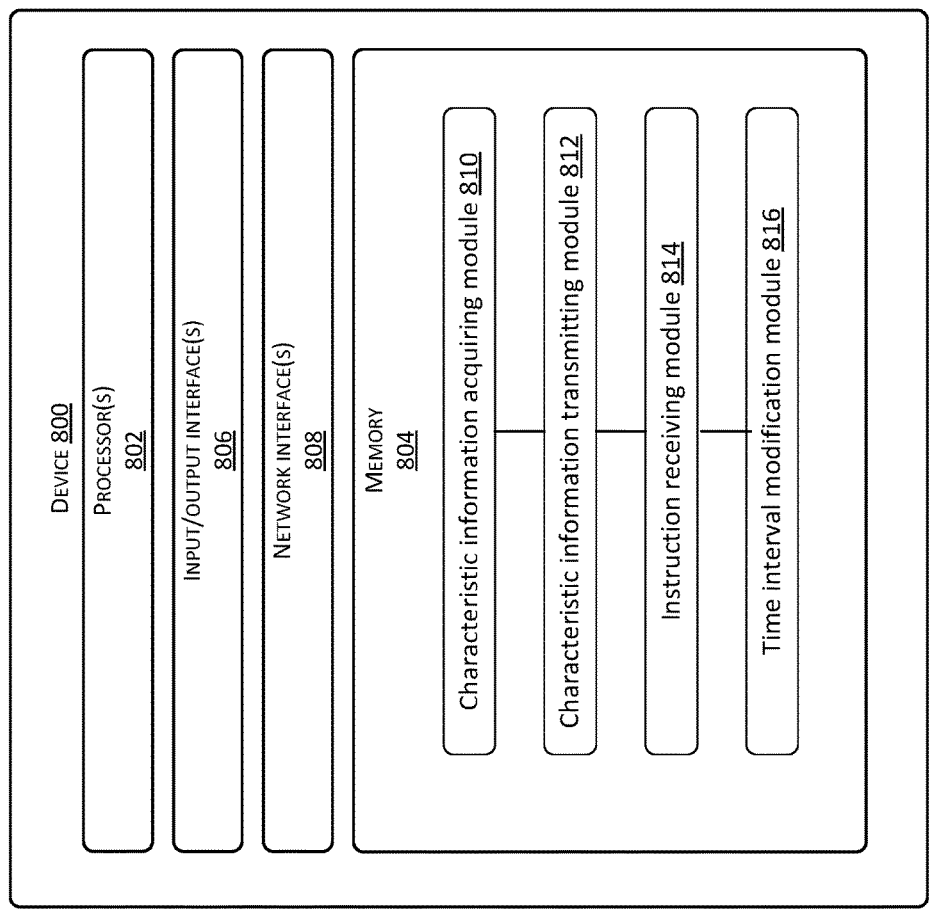
FIG. 8 is a schematic diagram illustrating a device for acquiring characteristic information in accordance with the implementations of the present disclosure.

FIG. 8 is a schematic diagram illustrating a device 800 for acquiring characteristic information in accordance with the implementations of the present disclosure.

The device 800 may include one or more processor(s) 802 or data processing unit(s) and memory 804. The device 800 may further include one or more input/output interface(s) 806, and network interface(s) 808. The memory 804 is an example of computer readable media.

The memory 804 may store therein a plurality of modules or units including a characteristic information acquiring module 810, a characteristic information transmitting module 812, an instruction receiving module 814, and a time interval modification module 816.

The characteristic information acquiring module 810 may be configured to acquire the characteristic information of a monitored party based on a predetermined time interval.

The characteristic information transmitting module 812 may be configured to transmit the characteristic information of the monitoring party to a server terminal.

The instruction receiving module 814 may be configured to receive an instruction to the monitored party to set a predetermined time interval for acquiring characteristic information as real-time access or an instruction to the monitored party to extend a predetermined time interval for acquiring characteristic information.

The time interval modification module 816 may be configured to change the time interval based on the acquired characteristic information of the monitoring party.

In implementations, the characteristic information acquiring module 810 may be configured to acquire current location information, current time information, and movement status information of the monitoring party based on the predetermined time interval if the monitored party is a mobile terminal.

In implementations, the device may further include an information receiving module configured to acquiring the characteristic information of the monitored party based on the predetermined time interval, receiving input of a gender, an age, and resident location information on the monitoring party.

In implementations, the device may further include a touch operation receiving module configured to receive a touch operation on an alarm area of the display and a three-strike operation on a power button after transmitting the characteristic information of the monitoring party to a server terminal. The alarm area may include an alarm area of a screen locking interface, or an alarm area of a desktop. The device may further include a current characteristic information obtaining module configured to acquire the characteristic information of the monitoring party, and an alarm information transmission module configured to transmit the alarm information to the server terminal. The alarm information may include the characteristic information of the monitoring party.

In implementations, the device may further include a third-party transmission module configured to transmit contact information to the monitored party and the alarm information to a map application.

In implementations, the characteristic information acquiring module 810 may be configured to acquire a heart rate, a body temperature, a respiratory rate and longitudinal acceleration of the monitoring party based on a predetermined time interval if the monitored party includes a smart device capable of monitoring health information.

In implementations, the device may further include an information receiving module configured to acquiring the characteristic information of the monitored party based on the predetermined time interval, receiving input of a gender and an age on the monitoring party.

In implementations, the device may further include a touch operation receiving module configured to receive a touch operation on an alarm area of the display and a two-strike operation on a power button after transmitting the characteristic information of the monitoring party to a server terminal. The alarm area may include an alarm area of a screen locking interface, or an alarm area of a desktop. The device may further include a current characteristic information obtaining module configured to acquire the characteristic information of the monitoring party, and an alarm information transmission module configured to transmit the alarm information to the server terminal. The alarm information may include the characteristic information of the monitoring party.

In implementations, the characteristic information acquiring module 810 may be configured to acquire a temperature, brightness, a volume, or a gas concentration of the monitoring party based on a predetermined time interval if the monitored party includes a sensor device capable of detecting a physical parameter.

In implementations, the device may further include a message receiving module configured to receive a prompt message generated based on characteristic information of the monitoring party to from the server terminal after transmitting the characteristic information of the monitoring party to a server terminal.

The above-described implementations relate to a method of security prejudgment based on characteristic information and a device for security prejudgment based on characteristic information, and an electronic device thereof, as well as a method of acquiring characteristic information and a device for acquiring characteristic information. In addition, the implementations further relate to an electronic device.

Figure 9:
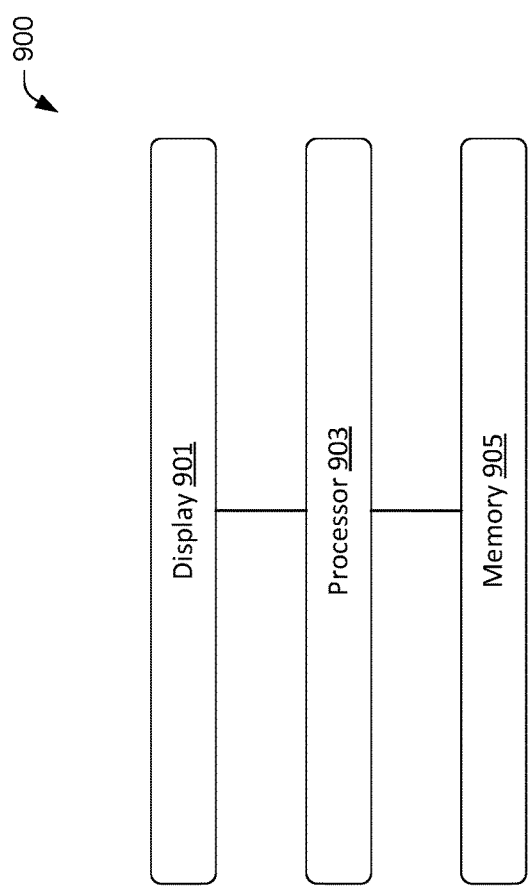
FIG. 9 is a schematic diagram illustrating another electronic device.

FIG. 9 is a schematic diagram illustrating an electronic device. The electronic device 900 may include a display 901, a processor 903, memory 905 configured to store a characteristic information acquiring program, executed by the one or more processors to acquire characteristic information of a monitored party based on a predetermined time interval, transmit the characteristic information of the monitoring party to a server terminal, receive an instruction to the monitored party to set a predetermined time interval for acquiring characteristic information as real-time access or an instruction to the monitored party to extend a predetermined time interval for acquiring characteristic information, and change the time interval based on the acquired characteristic information of the monitoring party. The memory 905 is an example of computer readable media.

The above-described implementations relate to a method of security prejudgment based on characteristic information and a device for security prejudgment based on characteristic information, and an electronic device thereof, as well as a method of acquiring characteristic information and a device for acquiring characteristic information. In addition, some implementations of the present disclosure relate to a system of security prejudgment based on the characteristic information.

Figure 10:
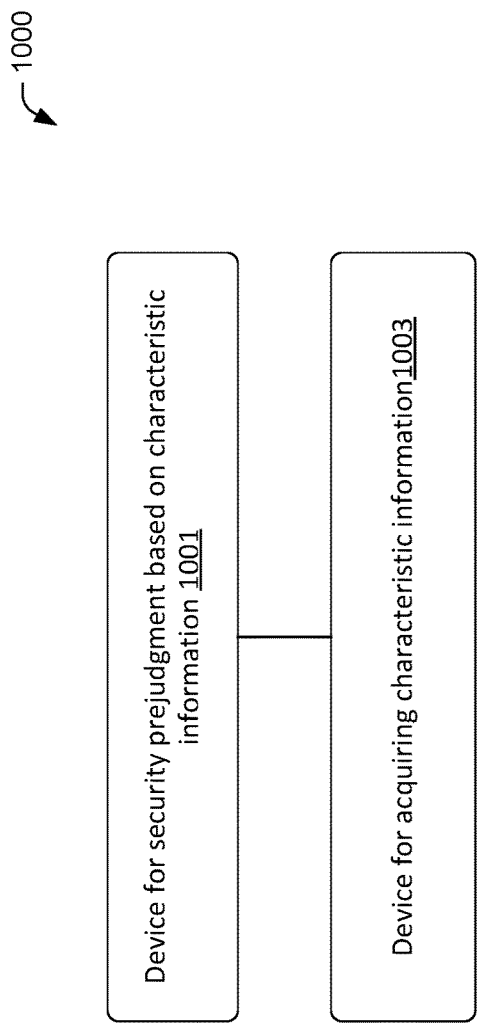
FIG. 10 is a schematic diagram illustrating a system for security prejudgment based on characteristic information in accordance with the implementations of the present disclosure.

FIG. 10 is a schematic diagram illustrating a system 1000 for security prejudgment based on characteristic information in accordance with the implementations of the present disclosure.

The system 1000 may include a device for security prejudgment based on characteristic information 1001, and a device for acquiring characteristic information 1003.

The device 1001 may receive characteristic information of a monitored party from the monitored party, calculate security status information of the monitored party based on a probability of danger that has been stored and corresponds to the characteristic information of the monitored party, determine that the security status information is greater than a first threshold, and perform an appropriate operation based on the determination, The device 1003 may acquire the characteristic information of a monitored party based on a predetermined time interval, transmit the characteristic information of the monitoring party to a server terminal, receive an instruction to the monitored party to set a predetermined time interval for acquiring characteristic information as real-time access or an instruction to the monitored party to extend a predetermined time interval for acquiring characteristic information, and change the time interval based on the acquired characteristic information of the monitoring party.

The device 1003 may be installed on a mobile terminal (e.g., a mobile phone or a tablet) including smart devices and sensor devices capable of detecting health information. it is not intended to limit these devices as long as they are capable of performing operations acquiring the characteristic information as described above. The device 1001 may be installed on a computing device, but not limited to the computing device, as long as they are capable of performing operations of security prejudgment based on the characteristic information as described above.

In a typical configuration, a computing device includes one or more processors (CPU), input/output interfaces, network interfaces, and memory.

Memory may include computer-readable medium volatile memory, random access memory (RAM) and/or nonvolatile memory, etc., such as read only memory (ROM) or flash memory (flash RAM). Memory is an example of computer readable media.

1. Computer readable media includes permanent and non-permanent, removable and non-removable media may be made in any method or technology to achieve information storage. Information can be computer-readable instructions, data structures, program modules or other data. Examples of computer storage media include, but not limited to phase-change memory (PRAM), static random access memory (SRAM), dynamic random access memory (DRAM), other types of random-access memory (RAM), read-only memory (ROM), electrically erasable programmable Read Only memory (EEPROM), flash memory or other memory technology, CD-ROM read-only memory (CD-ROM), digital versatile disc (DVD) or other optical storage, magnetic cassettes, magnetic disk storage or other magnetic tape storage devices, or any other magnetic non-transmission medium, which can be used to store the information for access by computing devices. Defined in accordance with this present disclosure, Computer readable media does not include non-transitory media, such as modulated data signal and carriers.

One skilled in the art should understand, embodiments of the present disclosure provide a method, system, or computer program product. Accordingly, the present disclosure may be entirely implemented by hardware, software, or a combination of hardware and software. Further, the present disclosure can be used in one or more computer usable storage media (including but not limited to the optical disk storage and memory, etc.) that contain computer usable program codes and are implemented on a computer program product.

Although the present disclosure provides preferred embodiments above, it is not intended to limit the present disclosure, one of ordinary skill in the art, without departing from the spirit and scope of the present disclosure, may make possible changes and modifications. Therefore, the scope of application should be defined by the scope of the claims of the present disclosure.

What is claimed is:

1. A method of security prejudgment, the method comprising:
   receiving characteristic information of a monitored party from the monitored party;
   calculating a security status information of the monitored party based on probabilities of danger that have been stored and correspond to the characteristic information of the monitored party, where the security status information is defined as a quantitative, prejudged state of security of the monitored party having a numerical value that varies according to the probabilities of danger associated with the characteristic information received from the monitored party, where the probabilities of danger include at least two of: current location information, current time information, movement status information, gender information, and age information;
   determining that the security status information is greater than a first threshold; and
   performing an appropriate operation based on the determination.

2. The method of claim 1, wherein the calculating the security status information of the monitored party based on the probabilities of danger that have been stored and correspond to the characteristic information of the monitored party includes a calculation based on Bayes' theorem using the at least two probabilities of danger.

3. The method of claim 2, wherein the performing the appropriate operation based on the determination comprises:
   transmitting to a predetermined monitoring party a login key used for acquiring the characteristic information of the monitored party if the security status information is greater than a first threshold; and
   transmitting a prompt message generated based on characteristic information of the monitoring party to the monitored party if the security status information is not greater than a first threshold.

4. The method of claim 3, wherein the transmitting to the predetermined monitoring party the login key used for acquiring the characteristic information of the monitored party comprises transmitting to the predetermined monitoring party the login key used for acquiring the characteristic information of the monitored party via an SMS text message.

5. The method of claim 3, further comprising:
   after transmitting to the predetermined monitoring party the login key used for acquiring the characteristic information of the monitored party,
   transmitting an instruction to the monitored party to set a predetermined time interval for acquiring characteristic information as real-time access.

6. The method of claim 3, further comprising:
   prior to the transmitting the prompt message generated based on the characteristic information of the monitored party to the monitored party,
   determining that the security status information is greater than a second threshold;
   transmitting the prompt message generated based on the characteristic information of the monitored party to the monitored party if the security status information is greater than a second threshold; and
   transmitting an instruction to the monitored party to extend a predetermined time interval for acquiring characteristic information if the security status information is not greater than a second threshold.

7. The method of claim 5, further comprising:
   after the receiving the characteristic information of a monitored party from the monitored party,
   receiving alarm information from the monitored party; and
   triggering and performing the operation of the transmitting to the predetermined monitoring party the login key used for acquiring the characteristic information of the monitored party.

8. The method of claim 2, wherein the monitored party is a mobile terminal, and the characteristic information of the monitored party comprises at least two of: current location information of the monitored party, current time information, movement status information of the monitored party, gender of the monitored party, and age of the monitored party.

9. The method of claim 8, wherein the calculating the security status information of the monitored party based on Bayes' theorem further includes:
   acquiring predetermined probabilities of danger corresponding to the current location information, the current time information, the movement status information, the gender, and the age in the characteristic information of the monitored party;
   introducing the at least two probabilities of danger into Bayes' theorem;
   calculating an overall probability of danger to the monitored party; and
   designating the overall probability of danger to the monitored party as the security status information of the monitored party.

10. The method of claim 9, wherein the calculating the security status information of the monitored party further includes:
    mapping the current location information in the characteristic information of the monitored party to resident location information of the monitored party;

starting a timer if the current location information is not within a predetermined range of the resident location information;

terminating the timer if the current location information is within a predetermined range of the resident location information; and in response to a determination that a time period recorded by the timer is greater than a predetermined time period, generating the overall probability of danger to the monitored party that is greater than the first threshold, and designating the overall probability of danger to the monitored party as the security status information of the monitored party.

11. The method of claim 8, further comprising:

after transmitting to a predetermined monitoring party a login key used for acquiring the characteristic information of the monitored party:

recording the current location information in the characteristic information of the monitored party;

designating the current location information as a trigger location information; and projecting each received current location information in the characteristic information of the monitored party onto a projection coordinate.

12. The method of claim 7, wherein the alarm information from the monitored party comprises at least one of: current location information of the monitored party, current time information, movement status information of the monitored party, a gender of the monitored party, or an age of the monitored party.

13. The method of claim 2, wherein the monitored party comprises a smart device capable of monitoring health information, and the characteristic information of the monitored party comprises at least one of a gender, an age, a heart rate, a body temperature, or a respiration rate.

14. The method of claim 13, wherein the calculating the security status information of the monitored party based on Bayes' theorem further includes:

acquiring predetermined probabilities of danger corresponding to the gender, the age, the heart rate, the body temperature and a respiration rate in the characteristic information of the monitored party;

introducing a probability of danger of the heart rate, a probability of danger of the body temperature, a probability of danger of the respiration rate, and the at least two probabilities of danger into Bayes' theorem;

calculating an overall probability of danger to the monitored party; and designating the overall probability of danger to the monitored party as the security status information of the monitored party.

15. The method of claim 14, wherein the characteristic information of the monitored party further comprises longitudinal acceleration with respect to the receiving the characteristic information of a monitored party from the monitored party, and wherein the calculating the security status information of the monitored party further includes acquiring a probability of danger corresponding to the longitudinal acceleration in the characteristic information of the monitored party.

16. The method of claim 7, wherein the alarm information from the monitored party comprises at least one of: a heart rate, a body temperature, or a respiratory rate.

17. The method of any of claim 2, wherein the monitored party comprises a sensor device capable of detecting a physical parameter, and wherein the characteristic information of the monitored party comprises at least one of a temperature, brightness, a volume or a gas concentration.

18. The method of claim 17, wherein the calculating the security status information of the monitored party based on Bayes' theorem further includes:

acquiring predetermined probabilities of danger corresponding to the temperature, the brightness, the volume, and the gas concentration in the characteristic information of the monitored party;

introducing a probability of danger of the temperature, a probability of danger of the brightness, a probability of danger of the volume, a probability of danger of the gas concentration, and the at least two probabilities of danger into Bayes' theorem;

calculating an overall probability of danger to the monitored party; and designating the overall probability of danger to the monitored party as the security status information of the monitored party.

19. A device for security prejudgment, the device comprising:

one or more processors; and a memory having instructions stored thereon, which when executed, cause the one or more processors to perform acts including:

receiving characteristic information of a monitored party from the monitored party, calculating a security status information of the monitored party based on probabilities of danger that have been stored and correspond to the characteristic information of the monitored party, where the security status information is defined as a quantitative, prejudged state of security of the monitored party having a numerical value that varies according to the probabilities of danger associated with the characteristic information received from the monitored party, where the probabilities of danger include at least two of: current location information, current time information, movement status information, gender information, and age information, determining that the security status information is greater than a first threshold, and performing an appropriate operation based on the determination.

20. One or more memories stored thereon computer-executable instructions, executable by one or more processors, to cause the one or more processors to perform acts comprising:

acquiring the characteristic information of a monitored party based on a predetermined time interval;

transmitting the characteristic information of the monitoring party to a server terminal;

calculating a security status information of the monitored party based on a probabilities of danger that have been stored and correspond to the characteristic information of the monitored party, where the security status information is defined as a quantitative, prejudged state of security of the monitored party having a numerical value that varies according to the probabilities of danger associated with the characteristic information received from the monitored party, where the probabilities of danger include at least two of: current location information, current time information, movement status information, gender information, and age information;

receiving an instruction to the monitored party to set a predetermined time interval for acquiring characteristic information as real-time access or an instruction to the monitored party to extend a predetermined time interval for acquiring characteristic information; and changing the time interval based on the acquired characteristic information of the monitoring party.

* * * * *